United States Patent [19]
Belanger et al.

[11] Patent Number: 5,135,940
[45] Date of Patent: Aug. 4, 1992

[54] LEUKOTRIENE ANTAGONISTS

[75] Inventors: Patrice C. Belanger, Dollard des Ormeaux; Joshua Rokach, Laval; Rejean Fortin, Montreal-Nord; Christiane Yoakim; Yvan Guindon, both of Montreal, all of Canada

[73] Assignee: Merck Frosst Canada, Inc., Kirkland, Canada

[21] Appl. No.: 672,520

[22] Filed: Mar. 20, 1991

Related U.S. Application Data

[63] Continuation of Ser. No. 253,992, Oct. 5, 1988, abandoned, which is a continuation of Ser. No. 877,655, Jun. 23, 1986, abandoned, which is a continuation-in-part of Ser. No. 591,346, Mar. 19, 1984, abandoned, which is a continuation-in-part of Ser. No. 520,052, Aug. 5, 1983, abandoned, which is a continuation-in-part of Ser. No. 422,338, Sep. 23, 1982, abandoned.

[51] Int. Cl.⁵ .............................................. A61K 31/41
[52] U.S. Cl. .................................... 514/381; 514/520; 514/544; 514/546; 514/571; 514/618; 514/621; 514/679; 548/253; 558/405; 560/9; 560/11; 560/53; 560/138; 562/426; 562/429; 562/463; 564/162; 564/169
[58] Field of Search ...................... 562/426, 429, 463; 560/9, 11, 53, 138; 564/162, 169; 568/31, 43, 29, 36, 37, 325; 514/381, 461, 475, 473, 520, 545, 570, 618, 685, 544, 546, 571, 621; 548/253; 558/405

[56] References Cited

U.S. PATENT DOCUMENTS

| | | | |
|---|---|---|---|
| 3,519,652 | 7/1970 | Fitzmaurice et al. | 424/303 |
| 3,676,449 | 7/1972 | Song | 548/142 |
| 3,704,327 | 11/1972 | Neuworth | 568/47 |
| 3,706,792 | 12/1972 | Shen et al. | 560/53 |
| 3,882,148 | 5/1975 | Augstein et al. | 549/402 |
| 3,899,513 | 8/1975 | Warren et al. | 549/402 |
| 3,943,169 | 3/1976 | Mufata et al. | 562/463 |
| 3,948,955 | 4/1976 | Lee et al. | 549/403 |
| 3,953,604 | 4/1976 | Warren et al. | 424/283 |
| 4,006,245 | 2/1977 | Augstein et al. | 424/283 |
| 4,058,558 | 11/1977 | Cousse et al. | 560/53 |
| 4,133,889 | 1/1979 | Augstein et al. | 424/269 |
| 4,213,903 | 7/1980 | Rantick et al. | 548/250 |
| 4,252,818 | 2/1981 | Rokach et al. | 424/283 |
| 4,393,075 | 7/1983 | Terao et al. | 514/519 |
| 4,423,048 | 12/1983 | Kadin | 544/250 |
| 4,499,299 | 2/1985 | Bernstein et al. | 514/570 |
| 4,507,498 | 3/1985 | Carson et al. | 560/53 |

FOREIGN PATENT DOCUMENTS

| | | |
|---|---|---|
| 043736 | 1/1982 | European Pat. Off. |
| 056172 | 7/1982 | European Pat. Off. |
| 080371 | 6/1983 | European Pat. Off. |
| 104885 | 4/1984 | European Pat. Off. |
| 0104885 | 4/1984 | European Pat. Off. |
| 0106565 | 4/1984 | European Pat. Off. |
| 0156233 | 10/1985 | European Pat. Off. |
| 0206741 | 12/1986 | European Pat. Off. |
| 1144905 | 3/1969 | United Kingdom |
| 1144906 | 3/1969 | United Kingdom |
| 1204122 | 9/1970 | United Kingdom |
| 1533820 | 11/1978 | United Kingdom |
| 2058785 | 4/1981 | United Kingdom |
| 2118184 | 10/1983 | United Kingdom |
| 2128999 | 5/1984 | United Kingdom |

OTHER PUBLICATIONS

Derwent Abstract 23065 K/10 (corresponds to French 2,509,725).
Young, et al., J. Med. Chem., 29, 1573–1576 (1986).

Primary Examiner—Michael L. Shippen
Attorney, Agent, or Firm—Gabriel Lopez; Joseph F. DiPrima

[57] ABSTRACT

Compounds of the Formulae:

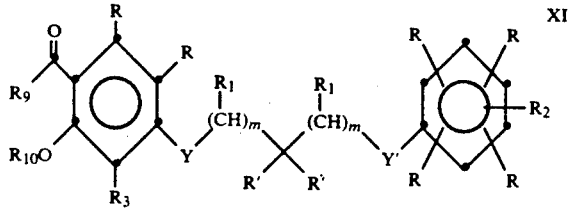

and

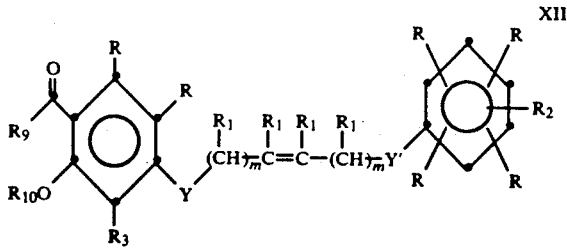

are antagonists of leukotrienes of $C_4$, $D_4$ and $E_4$, the slow reacting substance of anaphylaxis. These compounds are useful as anti-asthmatic, anti-allergic, anti-inflammatory, and cytoprotective agents.

13 Claims, No Drawings

LEUKOTRIENE ANTAGONISTS

REFERENCE TO RELATED APPLICATIONS

This application is a continuation-in-part of U.S. Ser. No. 591,346 filed Mar. 19, 1984, pending, which is a continuation-in-part of U.S. Ser. No. 520,052 filed Aug. 5, 1983, abandoned, which is a continuation-in-part of U.S. Ser. No. 422,338 filed Sep. 23, 1982, abandoned.

BACKGROUND OF THE INVENTION

Although the chemical identity of leukotrienes was not discovered until 1979, their history actually began in Australia in 1938 when researchers discovered slow reacting substances (SRS) which caused slow contractions of smooth muscle. When their chemical identity was learned, SRS was found to be a mixture of three previously unknown substances which are related chemically to the prostaglandins and thromboxanes. They were named leukotrienes because they are made by leukocytes and have three conjugated double bonds. Leukotrienes have major effects on the smaller peripheral airways of the lungs and on the larger central passages which include the trachea and the bronchi In the presence of an allergy trigger, like pollen or dust, leukotrienes are manufactured from fatty substances trapped in the membrane of a triggered cell. A series of reactions within the cell generates a set of different leukotrienes which are transported through the cell membrane into the blood. Then they bring about a constriction of the air passages leading to breathlessness.

OBJECTS OF THE INVENTION

It is an object of the present invention to provide compounds that act as antagonists to prevent leukotriene action or as inhibitors to prevent synthesis. A further object is to provide compounds which prevent or reverse leukotriene action or Prevent leukotriene synthesis when administered orally. Yet another object is to provide compounds which prevent or reverse leukotriene action or prevent leukotriene synthesis when administered by insufflation, intravenously, rectally, topically, parenterally including subcutaneously and intramuscularly, or nasally. Another object is to provide methods for the preparation of these compounds. A further object is to provide intermediates useful in the synthesis of these compounds. Still another object is to provide Pharmaceutical formulations for administering these compounds. These and other objects of the present invention will be apparent from the following description.

DETAILED DESCRIPTION

The present invention relates to compounds having activity as leukotriene antagonists, to methods for their preparation, to intermediates useful in their preparation and to methods for using these compounds. Because of their activity as leukotriene antagonists, the compounds of the present invention are useful as anti-asthmatic, anti-allergic, and anti-inflammatory agents and are useful in treating allergic rhinitis and chronic bronchitis and for amelioration of skin diseases like psoriasis and atopic exzema. These compounds are also useful to antagonize or inhibit the properties of leukotrienes relating to cardiovascular and vascular systems.

The compounds of the present invention have the Formulae:

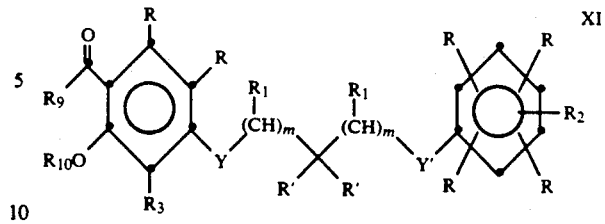

and

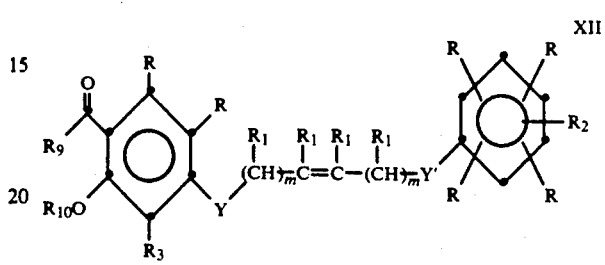

wherein each R is independently H, OH, alkyl of 1 to 6 carbon atoms which may be straight chain or branched; alkenyl of 2 to 6 carbon atoms which may be straight chain or branched; trifluoromethyl; alkoxy of 1 to 6 carbon atoms which may be straight chain or branched; SH; thioalkyl of 1 to 6 carbon atoms which may be straight chain or branched: phenyl phenyl substituted by alkyl of 1 to 3 carbon atoms or by halogen; benzyl; phenalkyl with from 2 to 4 alkyl carbon atoms; halogen, amino; $N(R_4)_2$ wherein $R_4$ is H or alkyl of 1 to 6 carbon atoms which may be straight chain or branched; $COOR_4$; $CH_2OR_4$; formyl; CN; trifluoromethylthio; or nitro;

each R' is independent $R_4$; $OR_4$; $COOR_4$; $N(R_4)_2$; $SR_4$; $CH_2OR_4$; CHO; or together R' and R' are O; $CH_2$; or

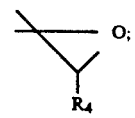

Y is oxygen, sulfur, sulfoxide, sulfone;

wherein $R_{11}$ is alkyl of 1–4 carbon atoms which may be straight chain or branched; $NR_{12}$ wherein $R_{12}$ is H, alkyl of 1–4 carbon atoms which may be straight chain or branched;

wherein $R_{13}$ is alkyl of 1–4 carbon atoms which may be straight chain or branched, alkoxy of 1–4 carbon atoms which may be straight chain or branched; or N—CN;

Y' is Y, —$CH_2$— or

each $R_1$ is independently hydrogen or alkyl of 1–3 carbon atoms;

each m is independently an integer from 0–6; and $R_2$ is

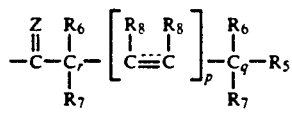

wherein is O, S, $CH_2$, H and OH, alkenyl of 1–4 carbons; or N—$R_{14}$ wherein $R_{14}$ is OH, alkyl or alkoxy of 1 to 6 carbon atoms, perhaloalkyl of 1 to 6 carbon atoms, phenyl or phenyl substituted by alkyl or alkoxy groups of 1 to 3 carbon atoms, halogen, hydroxy, haloalkyl, COOH, CN, formyl or acyl of 1 to 6 carbon atoms;

each $R_6$ is independently H or alkyl of 1–4 carbons;

each $R_7$ is independently H, OH, or alkyl of 1–4 carbons;

each $R_8$ is independently H, or alkyl of 1–4 carbons, and is absent when a triple bond is present;

$R_5$ is $COOR_4$; $CH_2OH$; CHO; tetrazole; $NHSO_2R_{14}$; $CONHSO_2R_{14}$; hydroxymethylketone; CN; $CON(R_7)_2$; a monocyclic or bicyclic heterocyclic ring containing an acidic hydroxyl group; or $COOR_{15}$ where $R_{15}$ is:

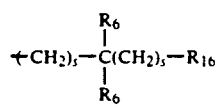

wherein each s is independently 0–3; $R_{16}$ is

A) a monocyclic or bicyclic heterocyclic radical containing from 3 to 12 nuclear carbon atoms and 1 or 2 nuclear heteroatoms selected from N and S with at least one being N, and with each ring in the heterocyclic radical being formed of 5 or 6 atoms, or B) the radical wherein W is O, S or NH and $R_{17}$ contains up to 21 carbon atoms and is (1) a hydrocarbon radical or (2) an acyl radical of an organic acyclic or monocyclic carboxylic acid containing not more than 1 heteroatom in the ring;

r and q are each independently 0–20 provided that the total of r and q does not exceed 20; and p is 0 or 1;

$R_3$ is H or alkyl of 1 to 6 carbon atoms which may be straight chain or branched; or alkenyl of 3 to 6 carbon atoms which may be straight chain or branched as illustrated in Formulae IV and V;

$R_9$ is alkyl of 1 to 6 carbon atoms which may be straight chain or branched; alkoxy of 1 to 6 carbon atoms which may be straight chain or branched; or $(CH_2)_rR_5$;

$R_{10}$ is H; alkyl of 1 to 6 carbon atoms which may be straight chain or branched;

or $R_4OCH_2$—;

and a pharmaceutically acceptable salt or acid addition salt thereof.

As used herein, the terms "each independently" or the equivalents thereof are employed to describe a number of possible position isomers and/or structural variations. For example, as described above, $R_2$ is:

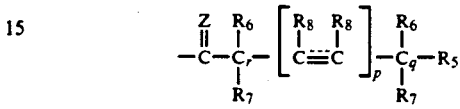

The letters r and q, represent possible alkane chains of from 0–20 carbon atoms, each having the $R_6$ and $R_7$ substituent groups. On each carbon atom of the alkane chain, the $R_6$ and/or $R_7$ substituent may be different. The above description therefore contemplates structures such as the following for the segments —$(CR_6R_7)_r$— and —$(CR_6R_7)_q$—:

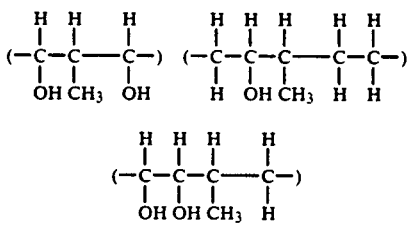

and the like.

It is understood that for those compounds which contain asymmetric centers, the present invention includes the racemic mixture as well as the individual resolved optical isomers.

A preferred embodiment of the present invention relates to compounds of the Formula XIa

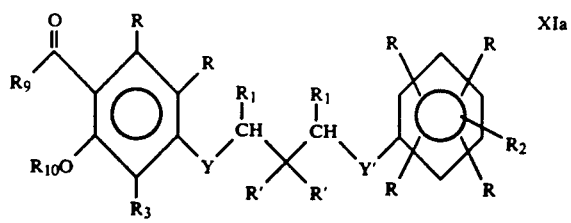

XIa wherein Y is oxygen and Y' is oxygen, sulfur, sulfoxide, sulfone, amino or cyanamido, and other substituents are as defined for Formula XI.

A more preferred embodiment relates to compounds of Formula XIa wherein $R_2$ is:

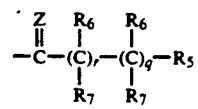

and wherein

Z is O, S, H and OH or N—$R_{14}$ where $R_{14}$ is as defined for Formula XI;

$R_5$, $R_6$ and $R_7$ are as defined for Formula XI;

r and q are each independently 0 to 5;

and the remaining substituents are as defined for Formula XI.

Another preferred embodiment of the present invention relates to compounds of the Formula XIb:

$$\text{XIb}$$

wherein:

Y is oxygen, Y' is oxygen, sulfur, sulfoxide or sulfone, each R' is independent $R_4$ wherein $R_4$ is as defined for XI $OR_4$ wherein $R_4$ is as defined for XI; $CH_2OR_4$ wherein $R_4$ is as defined for XI; or together R' and R' are O;

$R_2$ is wherein

Z is O, S, H and OH or N—$R_{14}$ wherein $R_{14}$ is as defined for Formula XI;

$R_5$, $R_6$ and $R_7$ are as defined for Formula XI;

r and q are each independently 0 to 5;

$R_9$ is alkyl of 1 to 6 carbon atoms which may be straight chain or branched;

$R_3$ is alkyl of 1 to 6 carbon atoms which may be straight chain or branched; and R is as defined for Formula XI.

A more preferred embodiment relates to compounds of Formula XIb wherein $R_5$ is $COOR_4$ or $COOR_{15}$ and $R_4$ and $R_{15}$ are as defined for Formula XI.

Another preferred embodiment of the present invention relates to compounds of Formula XIc and XIIc:

$$\text{XIc}$$

$$\text{XIIc}$$

wherein each R" is independently H; alkyl of 1 to 6 carbon atoms which may be straight chain or branched; alkenyl of 2 to 6 carbon atoms which may be straight chain or branched; trifluoromethyl; alkoxy of 1 to 6 carbon atoms which may be straight chain or branched; thioalkyl of 1 to 6 carbon atoms which may be straight chain or branched; phenyl; phenyl substituted by alkyl of 1 to 3 carbon atoms or by halogen; benzyl; phenalkyl with from 2 to 4 alkyl carbon atoms; halogen; $CH_2OR_4$ wherein $R_4$ is H or alkyl of 1 to 6 carbon atoms which may be straight chain or branched; $COOR_4$; formyl; CN; trifluoromethylthio; or nitro;

Y is oxygen;

Y' is oxygen, sulfur, sulfoxide, sulfone, amino or cyanamido;

and the other substituents are as defined for Formulae XI and XII.

A more preferred embodiment of the Formula XIc and XIIc compounds is that wherein:

$R_2$ is

Z is O, S, H and OH or N—$R_{14}$;

r and q are each independently 0 to 5;

and the remaining substituents are as defined for Formulae XIc and XIIc.

Among the preferred and more preferred embodiments described immediately above by Formulae XIc and XIIc, those embodiments of the present invention expressed by Formula XIc are preferred over XIIc.

Pharmaceutically acceptable salts of the compounds described herein are included within the scope of the present invention. Such salts may be prepared from pharmaceutically acceptable non-toxic bases including inorganic bases and organic bases. Salts derived from inorganic bases include sodium, potassium, lithium, ammonium, calcium, magnesium, ferrous, zinc, copper, manganous, aluminum, ferric, manganic salts and the like. Particularly Preferred are the potassium, sodium, calcium, and magnesium salts. Salts derived from pharmaceutically acceptable organic non-toxic bases include salts of primary, secondary and tertiary amines, substituted amines including naturally occurring substituted amines, cyclic amines and basic ion exchange resins, such as isopropylamine, tri-methylamine, diethanolamine, diethylamine, triethylamine, tripropylamine, ethanolamine, 2-dimethylaminoethanol, 2-diethylaminoethanol, tomethamine, lysine, arginine, histidine, caffeine, procaine, hydrabamine, choline, imidazole, betaine, ethylenediamine, glucosamine, methylglucamine, theobromine, purines, piperazine, N,N'-dibenzylethylenediamine, piperidine, N-ethylpiperidine, morpholine, N-ethylmorpholine, polyamine resins and the like.

The compounds of the present invention may be prepared by several different routes. According to one method a compound of Formula I is reacted with an optionally alkyl substituted alkenyl halide of Formula II wherein X is halogen and each $R_6$ is independently H or alkyl of 1-4 carbon atoms to yield the corresponding 2-hydroxy-4-alkenyloxy-acetophenone of Formula III. The compound of Formula III is then subjected to a Claisen rearrangement to yield a 2,4-dihydroxy-3-alkenyl-acetophenone compound of Formula IV. This rearrangement occurs on heating the compound of Formula III either neat or in a high boiling solvent, such as a halogenated hydrocarbon, e.g., dichlorobenzene, at from about 160° to about 210° C. The double bond in the compound of Formula IV may then be reduced, e.g., by catalytic hydrogenation with a catalyst such as Pd/C, to yield the corresponding saturated compound of Formula V.

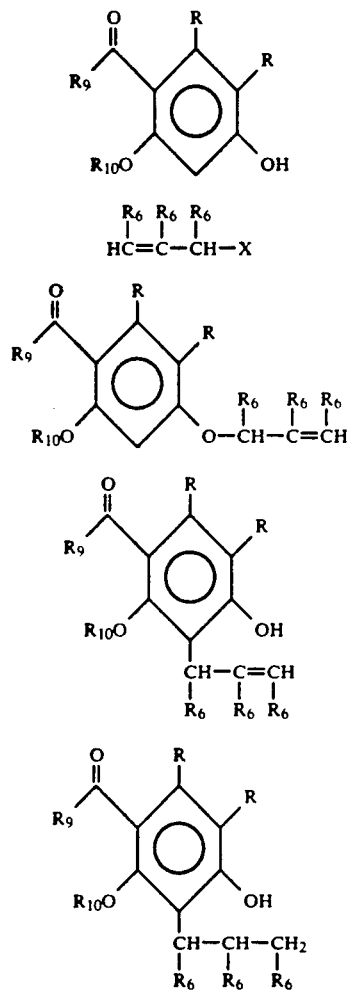

The compound of Formula V is then reacted with a dihaloalkane of Formula VIa or a dihaloalkene of Formula VIb wherein X, R and m have the meaning given previously, to yield a 4-(haloalkyloxy)-3-alkyl-2-hydroxyacetophenone compound of Formula VII. The reaction takes place by refluxing a mixture of the compounds of Formulae V and VIa or VIb in an inert solvent such as, for example, methylethylketone (MEK), acetone, tetrahydrofuran (THF), triglyme or dichloromethane in the presence of a base. The reflux temperature is preferably in the range of from about 60° to about 130° C. The base may be an alkali metal carbonate, for example, Li$_2$CO$_3$, Na$_2$CO$_3$ or K$_2$CO$_3$.

Specific examples of dihaloalkane compounds of Formula VIa are 1,3-dibromopropane, 2-methyl-1,3-dibromopropane 2,2-dimethyl-1,3-dibromopropane, 3-chloro-2-chloromethyl-1-propene, 1,3-dibromobutane, 1,4-dibromobutane, 1,5-dibromopentane, 1,6-dibromohexane, 1,7-dibromoheptane, 1,8-dibromooctane, 1,9-dibromononane, 1,10-dibromodecane, and 1,12-dibromododecane. A specific example of a dihaloalkene compound of Formula VIb is 1,4-dibromo-2-butene.

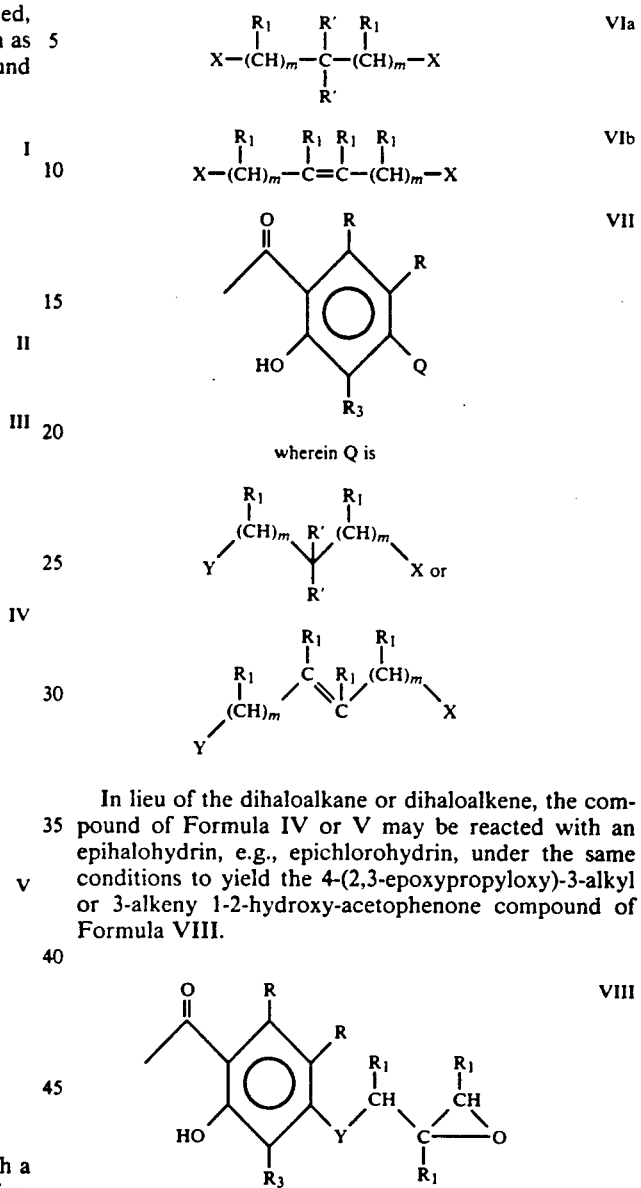

In lieu of the dihaloalkane or dihaloalkene, the compound of Formula IV or V may be reacted with an epihalohydrin, e.g., epichlorohydrin, under the same conditions to yield the 4-(2,3-epoxypropyloxy)-3-alkyl or 3-alkeny 1-2-hydroxy-acetophenone compound of Formula VIII.

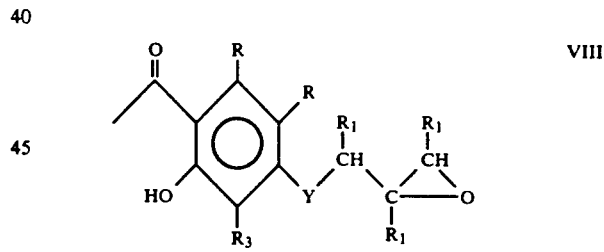

An alternative procedure is to react a compound of Formula II with a compound of Formula V to yield a 4-alkenyloxy-3-alkyl-2-hydroxy-acetophenone compound of Formula IX which is then epoxidized with an organic peracid such as, for example, m-chloroperbenzoic acid to give the compound of Formula VIII.

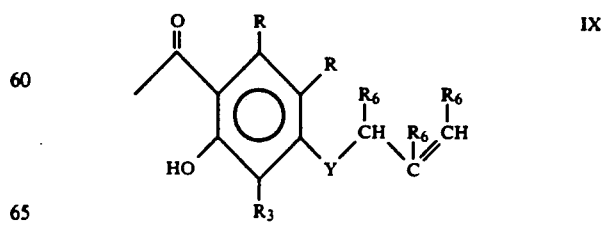

The reaction of a compound of Formula VII with a compound of Formula X, under the same conditions used to react a compound of Formula V with a compound of Formula VIa or VIb gives compounds of Formulae XI or XII.

The reaction of a compound of Formula VIII with a compound of Formula X under the same conditions used to react a compound of Formula V with a compound of Formula VIa or VIb gives a compound of Formula XI wherein each m is 1.

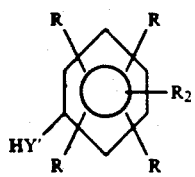    X

When Y' is —CH$_2$—, HY' is methyl. When Y' is

HY' is a protected aldehyde, such as, for example, a dithioacetal.

When Y$^1$ is methylene or carbonyl a stronger base such as, for example, lithium diisopropylamide or butyl lithium is employed in an inert solvent such as tetrahydrofuran with a suitable compound of Formula X.

A compound of Formula X is prepared by subjecting a compound of the Formula XIII:

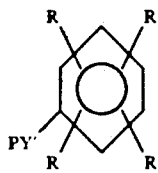    XIII wherein P is H or a protecting group such as, for example, methyl, benzyl, o-nitrobenzyl or 3-(m-nitrophenyl)-1-phenyl-1-oxo-3-propyl, to a Friedel-Crafts reaction with an acyl halide or an acid anhydride Other compounds of Formulae XI and XII are obtained by reacting a compound of Formula VII with a compound of Formula X under the same conditions used to react a compound of Formula V with a compound of Formula VIa or VIb.

Alternatively, the compounds of Formulae XI and XII may be prepared by reacting a compound of Formula X with a compound of Formula VIa or VIb or an epihalohydrin under the same conditions as described for the preparation of the compound of Formula VII to give a compound of the Formula XIVa, XIVb or XIVc respectively. The latter are then reacted under the same conditions with a compound of Formula V to give compounds of Formulae XI or XII.

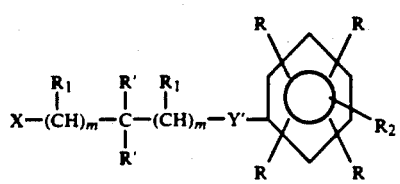    XIVa

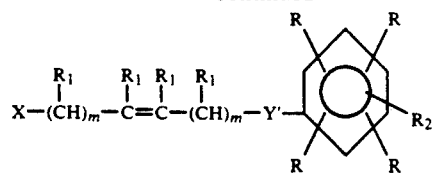    XIVb

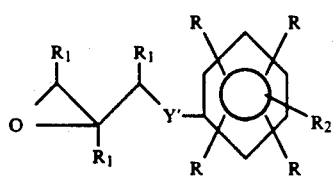    XIVc

Alternatively, but less preferably, the compounds of Formulae IV or V, X and either VIa, VIb or epihalohydrin may be reacted simultaneously under the conditions described above for reacting a compound of Formula VIa or VIb or epihalohydrin with a compound of Formula X.

Prodrug ester derivatives of the compounds of Formulae XI and XII may be prepared using conventional synthetic techniques available to the skilled artisan. For example, compounds of the Formula XV:

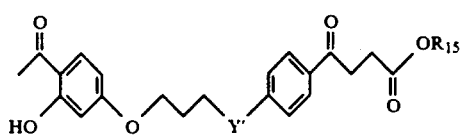    XV may be prepared as follows:

Method A:

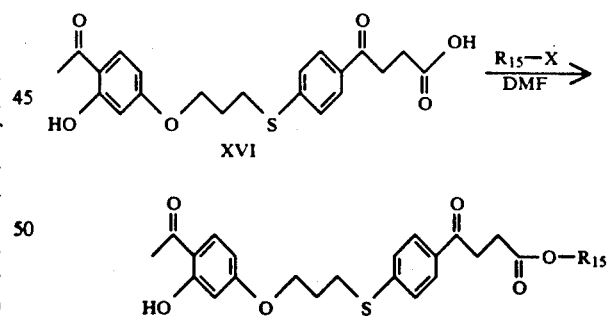

In Method A, the carboxylic acid of Formula XVI is reacted, in the presence of a base with an alkylhalide compound to provide the prodrug ester.

Method B:

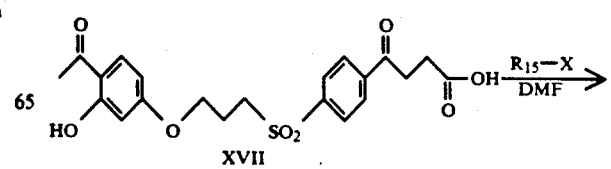

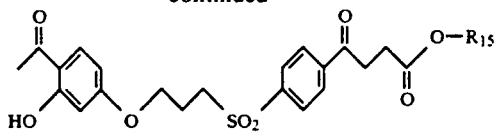

In Method B, the sulfone carboxylic acid of Formula XVII is similarly reacted with an appropriate alkylhalide, in the presence of base, to provide the corresponding prodrug ester.

Method C:

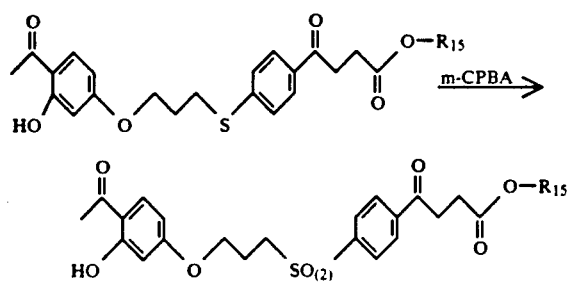

In Method C, the product of the Method A reaction, a prodrug ester, may be selectively oxidized to yield the sulfone or the sulfoxide compound.

In structures XI or XII, (Z=H+OH or $R_7$=OH and $R_5$=COOH, a lactone ring may be formed which would act as a prodrug form of the hydroxyacid. For example, a dehydration reaction of a compound having the Formula XVIII:

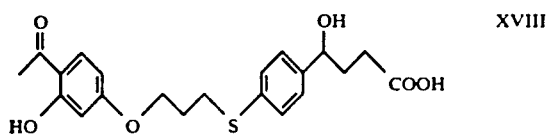

such as, by reaction with trifluoroacetic acid, would yield a lactone compound having the Formula XIX:

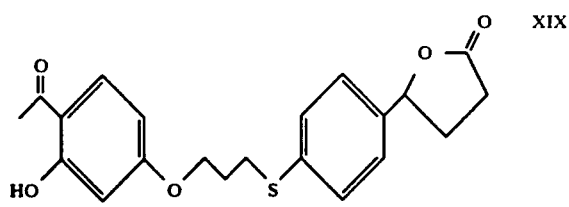

which when administered orally to a mammal would release the hydroxy acid form.

The magnitude of a prophylactic or therapeutic dose of a compound of Formula XI or XII will, of course, vary with the nature of the severity of the condition to be treated and with the particular compound of Formula XI or XII and its route of administration. In general, the daily dose range lies within the range of from about 0.2 mg to about 100 mg per kg body weight of a mammal.

The pharmaceutical compositions of the present invention comprise a compound of Formula XI or XII as an active ingredient, and may also contain a pharmaceutically acceptable carrier and optionally other therapeutic ingredients. The compositions include compositions suitable for oral, rectal, opthalmic, pulmonary, nasal, dermal, topical or parenteral (including subcutaneous, intramuscular and intravenous) administration, although the most suitable route in any given case will depend on the nature and severity of the conditions being treated and on the nature of the active ingredient. They may be conveniently presented in unit dosage form and prepared by any of the methods well-known in the art of pharmacy.

For use where a composition for intravenous administration is employed, a suitable dosage range is from about 0.01 to about 20 mg (preferably from about 0.1 to about 10 mg) of a compound of Formula XI or XII per kg of body weight per day and in the case where an oral composition is employed a suitable dosage range is, e.g. from about 1 to about 100 mg of a compound of Formula XI or XII per kg of body weight per day, preferably from about 5 to about 40 mg/kg.

For administration by inhalation, the compounds of the present invention are conveniently delivered in the form of an aerosol spray presentation from pressurized packs or a nebuliser. The preferred composition for inhalation is a powder which may be formulated as a cartridge from which the powder composition may be inhaled with the aid of a suitable device. In the case of a pressurized aerosol, the dosage unit may be determined by providing a valve to deliver a metered amount.

Pharmaceutical compositions of the present invention suitable for oral administration and by inhalation in the case of asthma therapy may be Presented as discrete units such as capsules, cachets or tablets each containing a Predetermined amount of the active ingredient, as a powder or granules, or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or moulding, optionally with one or more accessory ingredients. Compressed tablets may be prepared by compressing in a suitable machine, the active ingredient in a free-flowing form such as powder or granules, optionally mixed with a binder, lubricant, inert diluent, lubricating, surface active or dispersing agent. Moulded tablets may be made by moulding in a suitable machine, a mixture of the powdered compound moistened with an inert liquid diluent. Desirably, each tablet contains from about 25 mg to about 500 mg of the active ingredient and each cachet or capsule contains from about 25 to about 500 mg of the active ingredient.

The following are examples of representative pharmaceutical dosage forms for the compounds of Formula XI or XII:

| Injectable Suspension | mg/ml |
|---|---|
| Compound of Formula XI or XII | 2.0 |
| Methylcellulose | 5.0 |
| Tween 80 | 0.5 |
| Benzyl alcohol | 9.0 |
| Methyl paraben | 1.8 |
| Propyl paraben | 0.2 |

| -continued | |
|---|---|
| Water for injection to a total volume of | 1 ml |
| Tablet | mg/tablet |
| Compound of Formula XI or XII | 25.0 |
| Microcrystalline Cellulose | 415.0 |
| Providone | 14.0 |
| Pregelatinized Starch | 43.5 |
| Magnesium Stearate | 2.5 |
| | 500 |
| Capsule | mg/capsule |
| Compound of Formula XI or XII | 25.0 |
| Lactose Powder | 573.5 |
| Magnesium Stearate | 1.5 |
| | 600 |

In addition to the compounds of Formula XI and XII, the pharmaceutical compositions can also contain other active ingredients, such as cyclooxygenase inhibitors, non-steroidal anti-inflammatory drugs (NSAIDs), peripheral analgesic agents such as zomepirac diflunisal and the like. The weight ratio of the compound of the Formula XI or XII to the second active ingredient may be varied and will depend upon the effective dose of each ingredient. Generally, an effective dose of each will be used. Thus, for example, when a compound of the Formula XI or XII is combined with an NSAID, the weight ratio of the compound of the Formula XI or XII to the NSAID will generally range from about 200:1 to about 1:200. Combinations of a compound of the Formula XI or XII and other active ingredients will generally also be within the aforementioned range, but in each case, an effective dose of each active ingredient should be used.

Combinations of a compound of the Formula XI or XII and other active ingredients will generally be in the aforementioned ratios.

NSAIDs can be characterized into five groups:
(1) the propionic acid derivatives;
(2) the acetic acid derivatives;
(3) the fenamic acid derivatives; and
(4) the biphenylcarboxylic acid derivatives;
(5) the oxicams
or a pharmaceutically acceptable salt thereof The propionic acid derivatives which may be used comprise: ibuprofen, ibuprufen aluminum, indoprofen, ketoprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen and bucloxic acid. Structurally related proPionic acid derivatives having similar analgesic and anti-inflammatory properties are also intended to be included in this group.

Thus, "propionic acid derivatives" as defined herein are non-narcotic analgesics/non-steroidal anti-inflammatory drugs having a free —CH(CH$_3$)COOH or —CH$_2$CH$_2$COOH group (which optionally can be in the form of a pharmaceutically acceptable salt group, e.g., —CH(CH$_3$)COO$^-$Na$^+$ or —CH$_2$CH$_2$COO$^-$Na$^+$), typically attached directly or via a carbonyl function to a ring system, preferably to an aromatic ring system.

The acetic acid derivatives which may be used comprise: indomethacin, which is a preferred NSAID, sulindac, tolmetin, zomepirac, diclofenac, fenclofenac, alclofenac, ibufenac, isoxepac, furofenac, tiopinac, zidometacin, acemetacin, fentiazac, clidanac, oxpinac, and fenclozic acid. Structually related acetic acid derivatives having similar analgesic and antiinflammatory properties are also intended to be encompassed by this group.

Thus, "acetic acid derivatives" as defined herein are non-narcotic analgesics/non-steroidal anti-inflammatory drugs having a free —CH$_2$COOH group (which optionally can be in the form of a pharmaceutically acceptable salt group, e.g. —CH$_2$COO$^-$Na$^+$), typically attached directly to a ring system, preferably to an aromatic or heteroaromatic ring system.

The fenamic acid derivatives which may be used comprise: mefenamic acid, meclofenamic acid, flufenamic acid, niflumic acid and tolfenamic acid. Structurally related fenamic acid derivatives having similar analgesic and anti-inflammatory properties are also intended to be encompassed by this group.

Thus, "fenamic acid derivatives" as defined herein are non-narcotic analgesics/non-steroidal anti-inflammatory drugs which contain the basic structure:

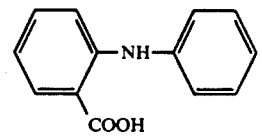

which can bear a variety of substituents and in which the free —COOH group can be in the form of a pharmaceutically acceptable salt group, e.g., —COO$^-$Na$^+$.

The biphenylcarboxylic acid derivatives which can be used comprise: diflunisal and flufenisal. Structurally related biphenylcarboxylic acid derivatives having similar analgesic and anti-inflammatory properties are also intended to be encompassed by this group.

Thus, "biphenylcarboxylic acid derivatives" as defined herein are non-narcotic analgesics/non-steroidal anti-inflammatory drugs which contain the basic structure:

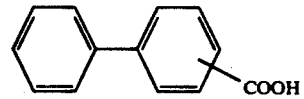

which can bear a variety of substituents and in which the free —COOH group can be in the form of a pharmaceutically acceptable salt group, e.g., —COO$^-$Na$^+$.

The oxicams which can be used in the present invention comprise: piroxicam, sudoxicam, isoxicam and 4-hydroxyl-1,2-benzothiazine 1,1-dioxide 4-(N-phenyl)-carboxamide. Structurally related oxicams having similar analgesic and anti-inflammatory properties are also intended to be encompassed by this group.

Thus, "oxicams" as defined herein are non-narcotic analgesics/non-steroidal anti-inflammatory drugs which have the general formula:

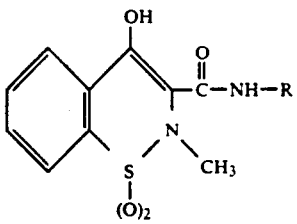

wherein R is an aryl or heteroaryl ring system.

The following NSAIDs may also be used: acemetacin, alminoprofen, amfenac sodium, aminoprofen, anitrazafen, antrafenine, auranofin, bendazac lysinate, benzydamine, beprozin, broperamole, bufezolac, carprofen, cinmetacin, ciproquazone, clidanac, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclofenac, fenclorac, fendosal, fenflumizole, fentiazac, feprazone, floctafenine, flunixin, flunoxaprofen, fluproquazone, fopirtoline, fosfosal, furcloprofen, furofenac, glucametacin, guaimesal, ibuproxam, isofezolac, isonixim, isoprofen, isoxepac, isoxicam, lefetamine HCl, leflunomide, lofemizole, lonazolac calcium, lotifazole, loxoprofen, lysin clonixinate, meclofenamate sodium, meseclazone, miroprofen, nabumetone, nictindole, nimesulide, orpanoxin, oxametacin, oxapadol, oxaprozin, perisoxal citrate, pimeprofen, pimetacin, piproxen, pirazolac, pirfenidone, pirprofen, pranoprofen, proglumetacin maleate, proquazone, pyridoxiprofen, sudoxicam, suprofen, talmetacin, talniflumate, tenoxicam, thiazolinobutazone, thielavin B, tiaprofenic acid, tiaramide HCl, tiflamizole, timegadine, tioxaprofen, tolfenamic acid, tolpadol, tryptamid, ufenamate, and zidometacin.

The following NSAIDs, designated by company code number, may also be used: 480156S, AA861, AD1590, AFP802, AFP860, AI77B, AP504, AU8001, BPPC, BW540C, CHINOIN 127, CN100, EB382, EL508, F1044, FZ, GV3658, ITF182, KCNTEI6090, KME4, LA2851, MR714, MR897, MY309, ON03144, PR823, PV102, PV108, R$_{830}$, RS2131, SCR152, SH440, SIR133, SPAS510, SQ27239, ST281, SY6001, TA60, TAI-901 (4, benzoyl-1-indancarboxylic acid), TEI615, TVX2706, U60257, and WY41770.

Finally, NSAIDs which may also be used include the salicylates, specifically aspirin, and the phenylbutazones, and pharmaceutically acceptable salts thereof.

Pharmaceutical compositions comprising the Formula XI or XII compounds may also contain inhibitors of the biosynthesis of the leukotrienes b such as are disclosed in EP 138,481 (Apr. 24, 1985), EP 115,394 (Aug. 8, 1984), EP 136,893 (Apr. 10, 1985), and EP 140,709 (May 8, 1985), which are hereby incorporated herein by reference.

The compounds of the Formula XI or XII may also be used in combination with leukotriene antagonists such as those disclosed in EP 56,172 (Jul. 21, 1982), 61,800 (Jun. 10, 1982), and 106,565 (Apr. 25, 1984); and in U.K. Patent Specification No. 2,058,785 (Apr. 15, 1981), which are hereby incorporated herein by reference.

Pharmaceutical compositions comprising the Formula XI or XII compounds may also contain as the second active ingredient, antihistaminic agents such as benadryl, dramamine, histadyl, phenergan and the like.

Alternatively, they may include prostaglandin antagonists such as those disclosed in EP Application 11,067 (May 28, 1980) or thromboxane antagonists such as those disclosed in U.S. Pat. No. 4,237,160. They may also Contain histidine decarboxyase inhibitors such as α-fluoromethylhistidine, described in U.S. Pat. No. 4,325,961. The compounds of the Formula XI or XII may also be advantageously combined with an $H_1$ or $H_2$-receptor antagonist, such as for instance cimetidine, ranitidine, terfenadine, famotidine, aminothiadiazoles disclosed in EP 40,696 (Dec. 2, 1981) and like compounds, such as those disclosed in U.S. Pat. Nos. 4,283,408; 4,362,736; and 4,394,508. The pharmaceutical compositions may also contain a $K^+/H^+$ ATPase inhibitor such as omeprazole, disclosed in U.S. Pat. No. 4,255,431, and the like. Each of the references referred to in this paragraph is hereby incorporated herein by reference.

The prodrug derivatives of the Formula XI or XII compounds may be substituted for such compounds in the pharmaceutical compositions discussed above, although in most instances the free carboxylic acid or a salt thereof is preferred.

ASSAY

Inhibition of LTD4-Induced Bronchoconstriction in Artificially Ventilated Anesthetized Guinea Pigs SPECIES: Guinea Pigs, male, 500 g (approx.), from Armand Frappier Inst.

METHOD: Guinea pigs were anesthetized with 1.5 g/kg of urethane given i.p.. Fifteen minutes later, the jugular vein, carotid artery and trachea were surgically cannulated. After surgery, the animals received a subcutaneous dose of 0.1 ml of succinylcholine chloride (2 mg/animal). When breathing became shallow, the guinea pig was connected to the respirator. Respiratory volume was adjusted to produce a tracheal pressure of 10 cm of $H_2O$ (10 mm deflection on the chart). Electrodes were placed for recording heart rate and the cannulated artery was connected to an appropriate transducer to monitor blood pressure. The animal was left to stabilize for 15 minutes before administration of mediators.

Schedule of Treatments for:

1) $LTD_4$ Dose Response Curve

After leaving the animal to stabilize for 15 minutes, the lowest dose of LTD was injected. If there was no response, the next higher dose of $LTD_4$ was injected after 15 minutes. When there was an increase in tracheal pressure following administration of $LTD_4$, the animal was hyperinflated by closing the outlet port of the respirator for 3 cycles. The hyperinflation maneuver reduced the tracheal pressure and facilitated the restoration of baseline values. The animal was hyperinflated at intervals of 7.5 minutes and successively increasing doses of $LTD_4$ were administered at 30 minute intervals. The dose response effects of $LTD_4$ on tracheal Pressure were evaluated using doubling doses of $LTD_4$ from 0.02–4.0 μg/kg. Each dose of $LTD_4$ was injected i.v. in 0.2 ml of saline followed by 0.2 ml of saline to flush the mediator through the tubing and cannula.

An appropriate amount of $LTD_4$ to give significant and reproducible increases in tracheal pressure was selected from the dose response curve. This dose was used to evaluate inhibitors, as described below. For the conditions and guinea pigs described above, 0.5 μg/kg of LTD$_4$ provided an appropriate dose.

A similar procedure was used for determining the dose response effects of other mediators on tracheal pressure. For example, histamine was administered in a range from 0.1–10 μg/kg.

2) Evaluation of Compounds—LTD$_4$ Antagonists

Each compound was evaluated against a dose of 0.5 μg/kg of LTD$_4$. Before testing the compound, the guinea pig was challenged until a constant increase in tracheal pressure was obtained from the administration of three successive doses of LTD$_4$. The guinea pig was hyperinflated as described between each dose of LTD$_4$. The compound was administered in 0.2 ml saline (or other solvent) and flushed in with 0.2 ml saline 2 minutes prior to the administration of LTD$_4$. The inhibition due to the compound was determined by the decreased elevation of tracheal pressure in comparison with controls.

By measuring the inhibition of LTD$_4$-induced elevation of tracheal pressure with increasing doses of the test compound, the dose which caused 50% inhibition could be obtained by linear regression.

3) Evaluation Compounds—Enzyme Inhibitors

Compounds of this type were evaluated in a protocol similar to 2 above except they were administered 15 minutes prior to LTD$_4$.

Representative compounds of the Formulae XI and XII were tested for their ability to alleviate leukotri D$_4$ induced bronchoconstriction in guinea pigs (i.v.). The median effective dose (ED$_{50}$) for these compounds are:

| | |
|---|---|
| Compound of Example 74B | 1 mg/kg |
| Compound of Example 74C | 0.21 mg/kg |
| Compound of Example 78 | 0.20 mg/kg |
| Compound of Example 82 | 1.45 mg/kg |

The following examples illustrate the present invention without, however, limiting the same thereto. All temperatures are expressed in degrees Celsius.

EXAMPLE 1

4-((3-(4-Acetyl-3-hydroxy-2-propylphenoxy)-2-hydroxypropyl)thio)-gamma-oxobenzenebutanoic acid A. Preparation of 4-methoxy-gamma-oxobenzenebutanoic Acid Anisole (70.0 g) and succinic anhydride (65.0 g) were dissolved in 1,2-dichloroethane (1 liter) and the mixture was cooled to 0° C. To the resulting suspension there was added, in portions, AlCl$_3$ (172 g) and the resulting mixture was stirred with a mechanical stirrer for 1 hour. The mixture was then poured into a mixture of ice and water (about 1 liter) containing 50 ml of concentrated HCl. The resulting white solid was collected by filtration, washed with water and air-dried to yield 4-methoxy-gamma-oxobenzenebutanoic acid, mp 145°–147° C.

B. Preparation of 4-hydroxy-gamma-oxobenzenebutanoic

A mixture of the compound from Step A (77.3 g), 48% HBr (310 ml), and acetic acid (620 ml) was heated under reflux for 18 hours. The resulting mixture was cooled to room temperature and poured into 3 liters of water. The resulting solution was combined organic layers were washed with water (4×200 ml), dried over Na$_2$SO$_4$, the solvents were removed by evaporation and the residue was dissolved in 10% HCl/methanol (500 ml). After 1 hour at room temperature the volatile components were removed by evaporation in vacuo. The resulting residue was triturated with hexane to yield the title compound, mp 115°–116°.

C. Preparation of 4-dimethylthiocarbamoyloxygamma-oxobenzenebutanoic acid, methyl ester A solution of the product from Step B, 25 g, in anhydrous dimethylformamide (DMF) (300 ml) was cooled to 0° and 99% NaH, 3.46 g, was added in two portions. The mixture was stirred for 1 hour at 0° then dimethylthiocarbamoyl chloride, 19.3 g, was added and the mixture heated at 90° under a N$_2$ atmosphere for 1.5 hours. The mixture was cooled to room temperature and diluted with water to 1,200 mL. The resulting solution was then extracted with ethyl acetate (3×500 ml). The combined organic layers were washed with brine and then dried over Na$_2$SO$_4$ and evaporated to dryness in vacuo to yield a residue which was purified by chromatography on silica gel to yield the title compound, mp 62°–64°.

D. Preparation of 4-dimethylcarbamoylthio-gamma-oxobenzenebutanoic acid, methyl ester The compound from Step C, 29.6 g, was heated at 200° for 10 hours under an N$_2$ atmosphere. The mixture was cooled to room temperature, dissolved in methylene chloride and purified by chromatography on silica gel to provide the title compound, mp 98°–100°.

E. Preparation of 4-mercapto-gamma-oxobenzenebutanoic acid, methyl ester

Sodium 280 mg, was dissolved in anhydrous methanol, 50 ml, under an N$_2$ atmosphere. To the resulting solution there was added 5.0 g of the compound from Step D. The mixture was stirred at room temperature overnight, then poured into a mixture containing 30 ml of water and 7 ml of concentrated HCl. The resulting yellow solid was collected by filtration, washed with water and dried in air to give the title compound, mp 83°–84°.

F. Preparation of 4-((3-(4-acetyl-3-hydroxy-2-propylphenoxy)-2-hydroxypropyl)thio)-gamma-oxobenzenebutanoic acid 2-Hydroxy-3-propyl-4-(2,3-epoxypropoxy)acetophenone (J. Med. Chem., 20, 371–379 (1977)) (0.6 g, 2.4 mmole) was refluxed in 15 ml of methylethyl ketone with the product from step E (0.6 g, 2.4 mmole) for two days in t he presence of 1.0 equivalent of K$_2$CO$_3$. The product was purified by chromatography on silica gel. The product, 0.9 g was saponified with KOH (1.5 equivalents) in a 25 ml mixture of methanol and water (10:1). The volatile components were removed under vacuum. The residue was taken up in water and acidified with citric acid. The aqueous phase was extracted twice with ethyl acetate, the organic layer was washed with brine, dried (Na and evaporated to dryness to leave the acid residue which was triturated in hexane and filtered Analysis, Calculated: C, 62.18; H, 6.74. Observed: C, 62.14, H, 6.32.

EXAMPLE 2

4-((3-(4-Acetyl-3-hydroxy-2-propylphenoxy)-2-hydroxypropyl)thio)-2fluoro-gamma-oxobenzenebutanoic acid Following the procedure of Example 1 but substituting an equivalent amount of 3-fluoroanisole for anisole in Step A, the title compound was obtained, mp 136–137°.

EXAMPLE 3

4-((3-(4-Acetyl-3-hydroxy-2-propylphenoxy)-2-hydroxypropyl)thio)-3-fluoro-gamma-oxobenzenebutanoic acid Following the procedure of Example 1 but substituting an equivalent amount of 2-fluoroanisole for anisole in Step A, the title compound was obtained, m.p. 106°-109° C.

EXAMPLE 4

Methyl 4-((3-(4-acetyl-3-hydroxy-2-Propylphenoxy)-2-hydroxypropyl)thio)-2-hydroxy-gamma-oxobenzene butanoate A. Preparation of 3-(3-nitrophenyl)-3-(3-methoxyphenylthio)-1-phenyl-1-propanone Piperidine, 1.2 ml, was added to a boiling solution of 3-nitrobenzalacetophenone (10 g, 0.04 mole) and 3-methoxybenzenethiol (6.64 g, 0.048 mole) in 100 ml benzene. After standing for 30 minutes without further heating, acetic acid, 10 ml, was added. The solution then was poured into water (about 100 ml), extracted with methylene chloride (5×100 ml), washed with water, dried ($Na_2SO_4$) and evaporated to dryness to yield the title compound as a solid, mp 105°.

B. Preparation of 4-(3-phenyl-3-oxo-1-(3-nitrophenyl)-1-propylthio)-2-hydroxy-gamma-oxobenzenebutanoic acid, methyl ester Succinic anhydride (11.45 g, 0.11 mole) was dissolved in 1,2-dichloroethane (300 ml) and $AlCl_3$ (50.76 g, 0.38 mole) was added under $N_2$. The resulting mixture was stirred for 3 hours at room temperature, cooled to 0° C. and the compound from Step A (13 g, 0.03 mole), dissolved in 1,2-dichloroethane, was added slowly. The reaction mixture was kept at 5° C. for 3 days, then poured on ice, stirred for one hour and the two phases separated by decanting. The aqueous phase was extracted several times with $CH_2Cl_2$ (600 ml total). The organic phases were combined, washed with water, dried ($MgSO_4$) and evaporated to dryness to yield the title compound as the free acid which then was converted to the methyl ester in conventional manner by treating the acid with methanol and anhydrous HCl. The ester had the following analysis: calculated: C, 63.27; H, 4.70; S, 6.50; observed: C, 63.19; H, 4.81; S, 6.63.

C. Preparation of 4-mercapto-2-hydroxy-gamma-oxobenzenebutanoic acid, methyl ester To a well stirred solution of the ester from Step B (1.0 g, 2.02 mmoles) in a mixture of CHCl (20 ml) and $C_2H_5OH$ (20 ml) was added lead acetate trihydrate (6 equivalents). After stirring the solution for 15 minutes, 10% NaOH was added to maintain the pH at 9-10. A yellow precipitate formed. After stirring for three hours, the suspension was filtered and washed with $CHCl_3$. The solid was taken up in methanolic HCl (10 ml), stirred for one hour and evaporated to dryness. The residue was taken up in ethyl acetate, the white solid was filtered off and the filtrate evaporated to dryness to yield the title compound calculated: C, 54.98, H, 5.04, S, 13.35; observed: C, 55.10, H, 4.94, S, 3.21.

D. Preparation of methyl 4-((3-(4-acetyl-3-hydroxy-2-propylphenoxy)-2-hydroxypropyl) thio)-2-hydroxy-gamma-oxobenzenebutanoate Following the procedure of Step F of Example but substituting an equivalent amount of the ester from Step C above for 4-mercapto-gamma-oxobenzenebutanoic acid, methyl ester, the title compound was obtained.

Analysis, calculated: C, 61.21; H, 6.16. Observed: C, 61.13; H, 6.30.

EXAMPLE 5

4-((3-(4-Acetyl-3-hydroxy-2-propylphenoxy)-2-hydroxypropyl)thio)-2-hydroxygamma-oxobenzenebutanoic acid The compound prepared according to Example 4 (544 mg, 1.15 mmol) was refluxed with $NaHCO_3$ (482 mg, 5.75 mmole) in a 20 ml mixture of methanol and water (3:1) for 4 hours. Then IN hydrochloric acid was added and the mixture was extracted with CH washed with water, dried ($Na_2SO_4$), and evaporated to dryness to yield a residue which was recrystallized from methanol/hexane, mp 149.5°. Analysis, calculated: C, 62.45; H, 6.33; S, 6.95. Observed: C, 62.46, H, 6.37; S, 7.24.

EXAMPLE 6

4-((3-(4-Acetyl-3-hydroxy-2-propylphenoxy)propyl)thio)-gamma-oxobenzenebutanoic acid Following the procedure of Step F of Example 1 but substituting an equivalent amount of 2-hydroxy-3-propyl-4-(3-bromopropyloxy)acetophenone (J. Med. Chem., 20, 371-379 (1977)) for 2-hydroxy-3-propyl-4-(2,3-epoxypropoxy)acetophenone, the title compound was obtained.

Analysis, calculated: C, 64.98; H, 6.14; S, 7.23. Observed: C, 65.09; H, 6.09; S, 7.28.

EXAMPLE 7

4-((3-(4-Acetyl-3-hydroxyphenoxy)propylthio)-gamma-oxobenzenebutanoic acid

Following the procedure of Step F of Example 1, but substituting 2-hydroxy-4-(3-bromopropyloxy) acetophenone for 2-hydroxy-3-propyl-4-(2,3-epoxypropoxy)acetophenone, the title compound was obtained.

Analysis, calculated: C, 62.66; H, 5.51; S, 7.96. Observed: C, 62.72; H, 5.64; S, 7.90.

EXAMPLE 8

4-((3-(4-Acetyl-3-hydroxy-2-propylphenoxy)propyl)thio)-2-hydroxy-gamma-oxobenzenebutanoic acid A. Preparation of methyl ester of 4-((3-(4-acetyl-3-hydroxy-2-propylphenoxy)propyl)thio)-2-hydroxy-gamma-oxobenzenebutanoic acid Following the procedure of Step F of Example 1 but substituting an equivalent amount of 2-hydroxy-3-propyl-4-(3-bromopropyloxy)acetophenone for 2-hydroxy-3-propyl-4-(2,3-epoxypropoxy)acetophenone and substituting an equivalent amount of the product from Step C of Example 4 for 4-mercapto-gamma-oxobenzenebutanoic acid, methyl ester, the title compound was obtained.

Analysis, calculated: C, 63.27; H, 6.37; S, 6.76. Observed: C, 63.30; H, 6.54; S, 6.70.

B. Preparation of 4-((3-(4-acetyl-3-hydroxy-2-propylphenoxy)propyl)thio)-2-hydroxy-gamma-oxobenzenebutanoic acid By treating the product from Step A of this example according to the procedure of Example 5, the title compound was obtained, mp 140° C.

Analysis, calculated: C, 62.59; H, 6.13; S, 6.96. Observed: C, 62.34; H, 6.47; S, 7.19.

EXAMPLE 9

4-((3-(4-Acetyl-3-hydroxy-2-propylphenoxy)-2-hydroxypropyl)thio)-2-methoxy-gamma-oxobenzenebutanoic acid A. Preparation of 4-mercapto-2-methoxy-gamma-oxobenzenebutanoic acid, methyl ester The free acid from Step B of Example 4 was dissolved in $CH_3OH$ and treated with excess diazomethane at room temperature. Volatiles were removed under vacuum. After purification on silica gel, there was obtained the methyl ester of 4-(3-phenyl-3-oxo-1-(m-nitrophenyl)-1-propylthio)-2-methoxy-gamma-oxobenzenebutanoic acid. This ester was reacted with lead acetate trihydrate to yield 4-mercapto-2-methoxy-gamma-oxobenzenebutanoic acid. The methyl ester of the acid was obtained in conventional manner by treatment with methanolic HCl.

B. Preparation of 4-((3-(4-acetyl-3-hydroxy-2-propylphenoxy)-2-hydroxypropyl)thio)-2-methoxy-gamma-oxobenzenebutanoic acid Following the procedure of Step F of Example 1 but substituting an equivalent amount of the ester from Step A of this example for 4-mercapto-gamma-oxobenzenebutanoic acid, methyl ester, the title compound was obtained.

Analysis, calculated: C, 61.20; H, 6.16; S, 6.53. Observed: C, 61.14; H, 6.26; S, 6.51.

EXAMPLE 10

4-((3-(4-Acetyl-3-hydroxy-2-propylphenoxy)-propyl)thio-3-fluoro-gamma-oxobenzenebutanoic acid Following the procedure of Example 1 but substituting an equivalent amount of 2-fluoroanisole for anisole in Step A and substituting an equivalent amount of 2-hydroxy-3-propyl-4-(3-bromopropoxy)acetophenone for 2-hydroxy-3-propyl-4-(2,3-epoxypropoxy)acetophenone in Step F, the title compound was obtained, m.p. 115°–116° C.

EXAMPLE 11

4-((3-(4-Acetyl-3-hydroxy-2-propylphenoxy)propyl)-thio)-2-fluoro-gamma-oxobenzenebutanoic acid Following the procedure of Example 10 but substituting 3-fluoroanisole for 2-fluoroanisole, the title compound was obtained, mp 149°–150° C.

EXAMPLE 12

4-(3-(4-Acetyl-3-hydroxy-2-propylphenoxy)propoxy)-3-fluoro-gamma-oxobenzenebutanoic acid A. Preparation of 4-Hydroxy-3-fluoro-gamma-oxobenzenebutanoic acid, methyl ester To a solution of 2-fluorophenol (22.4 g, 200 mmole) in 1,2-dichloroethane (250 ml) at 0° there was added $AlCl_3$ (54 g, 400 mmole) and then succinic anhydride (20 g, 200 mmole). The reaction mixture was heated at 85° C. for 18 hours, then cooled, poured on ice and stirred for several hours at room temperature. The layers were separated and the aqueous layers extracted with $CH_2Cl_2$. The combined extracts were washed with water, dried ($MgSO_4$) and evaporated to a semi-solid which was taken up in a solution of methanolic HCl (500 ml, approximately 3N). After standing for 24 hours the solution was poured into water, extracted with $CH_2Cl_2$, washed with water, dried and evaporated to a small volume. The crude product was purified by chromatography on silica gel to yield the title compound.

Analysis, calculated: C, 58.41; H, 4.91; F, 8.40. Observed: C, 58.63;, H, 4.96; F, 8.14. Its isomer, 2-hydroxy-3-fluoro-gamma-oxobenzenebutanoic acid, methyl ester, was also isolated in the chromatographic step.

Analysis, calculated: C, 58.41; H, 4.91; F, 8.40. Observed: C, 58.53; H, 4.82; F, 8.10.

B. Preparation of 4-(3-(4-acetyl-3-hydroxy-2-propylphenoxy)propoxy)-3-fluoro-gamma-oxobenzenebutanoic acid Following the procedure of Example 6 but substituting the title ester from Step A of this example for 4-mercapto-gamma-oxobenzenebutanoic acid, methyl ester, the title compound was obtained, m.p. 142°–144° C.

Analysis, calculated: C, 64.56; H, 6.10; F, 4.26. Observed: C, 64.74, H, 6.15; F, 4.55.

C. Preparation of 2-(3-(4-acetyl-3-hydroxy-2-propylphenoxy)propoxy)-3-fluoro-gamma-oxobenzenebutanoic acid Following the procedure of Step B of this example but substituting 2-hydroxy-3-fluoro-gamma-oxobenzenebutanoic acid, methyl ester for 4-hydroxy-3-fluoro-gamma-oxobenzenebutanoic acid, methyl ester, the title compound was obtained.

Analysis, calculated: C, 64.56; H, 6.10; F, 4.26. Observed: C, 64.41, H, 6.22; F, 4.24.

EXAMPLE 13

4-(3-(4-Acetyl-3-hydroxy-2-Propylphenoxy)propoxy)-3-fluoro-epsilon-oxobenzenehexanoic acid A. Preparation of 4-hydroxy-3-fluoro-epsilon-oxobenzenehexanoic acid, methyl ester Following the procedure of Example 12 but adding $TiCl_4$ (2.5 ml, 21.8 mmole) at −15° C. in lieu of $AlCl_3$ in Step A and substituting methyl 5-chloroformylpentanoate (3.57 g, 20 mmole) for succinic anhydride, and then heating the reaction mixture to 90° C. for 3 hours, the title compound was obtained.

Analysis, calculated: C, 61.51; H, 5.45; F, 7.47. Observed: C, 61.51 H, 6.14: F, 7.0B. Its isomer, 2-hydroxy-3-fluoro- -epsilon-oxobenzenehexanoic acid, methyl ester, was also obtained, m.p. 59°–60° C. Analysis, calculated: C, 61.41; H, 5.95; F, 7.47. Observed: C, 61.58; H, 6.05; F, 7.17.

B. Preparation of 4-(3-(4-acetyl-3-hydroxy-2-propylphenoxy)propoxy)-3-fluoro-epsilon-oxobenzenehexanoic acid Following the procedure of Step B of Example 2, but substituting the title ester from Step A of this example for 4-hydroxy-3-fluoro-gamma-oxobenzenebutanoic acid, methyl ester, the title compound was obtained, m.p. 106°–107° C.

Analysis, calculated: C, 65.81; H, 6.59; F, 4.00. Observed: C, 65.90; H, 6.18; F, 3.71.

C. Preparation of 2-(3-(4-acetyl-3-hydroxy-2-propylphenoxy)propoxy)-3-fluoro-epsilon-oxobenzenehexanoic acid Following the procedure of step B of this example but substituting 2-hydroxy-3-fluoro-epsilon-oxobenzenehexanoic acid, methyl ester for the title compound of Step A of this example, the title compound was obtained.

Analysis, calculated: C, 65.81; H, 6.59; F, 4.00. Observed: C, 65.90; H, 6.13; F, 3.71.

EXAMPLE 14

4-(3-(4-Acetyl-3-hydroxy-2-propylphenoxy)propoxy)-2-fluoro-gamma-oxobenzenebutanoic acid Following the procedure of Steps A and B Example 12 but substituting an equivalent amount of 3-fluorophenol for 2-fluorophenol in Step A, the title compound was obtained, m.p. 113°–118° C.

EXAMPLE 15

4-(3-(4-Acetyl-3-hydroxy2-propylphenoxy)propoxy)-gamma-oxobenzenehutanoic acid

By reacting the compound of Step B of Example 1 with 2-hydroxy-3-propyl-4-(3-bromopropyloxy)acetophenone according to the procedure of Step F of Example 1, the title compound was obtained.

Analysis, calculated: C, 67.27; H, 6.58. Observed: C, 67.30; H, 6.56.

EXAMPLE 16

4-(3-(4-Acetyl-3-hydroxy-2-propylphenoxy)propoxy)-2,3-dichloro-gamma-oxobenzenebutanoic acid Following the procedure of Steps A and B of Example 1, but substituting 2,3-dichloroanisole for anisole in Step A, there was obtained 2,3-dichloro-4-hydroxy-gamma-oxobenzenebutanoic acid, methyl ester. The ester was reacted with 2-hydroxy-3-propyl-4-(3-bromopropyloxy)acetophenone according to the procedure of Step F of Example 1 to give the title compound, mp 119°–123° C.

EXAMPLE 17

4-(3-(4-Acetyl-3-hydroxy-2-propylphenoxy)propoxy)-3methyl-gamma-oxobenzenebutanoic acid Following the Procedure of Example 16, but substituting 2-methyl anisole for 2,3-dichloro anisole there was obtained 3-methyl-4-hydroxy-gamma-oxobenzenebutanoic acid, methyl ester. The ester then was reacted with 2-hydroxy-3-propyl-4-(3-bromopropyloxy)acetophenone according to the procedure of Step F of Example 1 to give the title compound, mp 179°–180° C.

Analysis, calculated: C, 67.86; H, 6.83. Observed: C, 6.83; H, 6.80.

EXAMPLE 18

4-(3-(4-Acetyl-3-hydroxy-2-propylphenoxy)propoxy)-2-chloro-gamma-oxobenzenebutanoic acid Following the procedure of Example 16 but substituting 3-chloroanisole for 2,3-dichloroanisole, there was obtained 2-chloro-4-hydroxy-gamma-oxo-benzenebutanoic acid, methyl ester. The ester then was reacted with 2-hydroxy-3-propyl-4-(3-bromo-propyloxy)acetophenone according to the procedure of Step F of Example 1 to give the title compound, mp 143°–144.5° C.

Analysis, calculated: C, 62.27; H, 5.88; Cl, 7.66. Observed: C, 62.14; H, 5.92; Cl, 7.89.

EXAMPLE 19

4-(4-(4-Acetyl-3-hydroxy-2-propylphenoxy)-2-butenoxy)-3-fluoro-qamma-oxobenzenebutanoic acid Following the procedure of Step F of Example 1 but substituting 2-hydroxy-3-propyl-4-(4-chloro-2-butenoxy)acetophenone for 2-hydroxy-3-propyl-4-(2,3-epoxypropoxy)acetophenone, and substituting 4-hydroxy-3-fluoro-gamma-oxobenzenebutanoic acid, methyl ester for the methyl ester product of Step E of Example 1, the title compound was obtained, mp 170°–171.5° C.

Analysis, calculated: C, 65.49; H, 5.94; F, 4.14. Observed: C, 65.58; H, 6.02; F, 4.22.

EXAMPLE 20

4-(3-(4-acetyl-3-hydroxy-2-propylphenoxy)propoxy-3-propyl-gamma-oxobenzenebutanoic acid Following the procedure of Example 17 but substituting 2-n-propyl anisole for 2-methylanisole, the title compound was obtained.

Analysis, calculated: C, 67.27; H, 6.58. Observed: C, 67.30; H, 6.54.

EXAMPLE 21

4-(3-(4-Acetyl-3-hydroxy-2-propylphenoxy)-2-hydroxypropylthio)-3-fluoro-gamma-oxobenzenebutanoic acid-S-oxide The ester prepared according to the procedure of Example 3 was dissolved in 50 mL $CH_2Cl_2$, the solution was cooled to 0° and 1 equivalent of m-chloroperbenzoic acid was added. The reaction mixture was stirred at 0° C. for 5 minutes and was purified by chromatography on silica gel to yield the methyl ester of the title compound, that was saponified by stirring with sodium hydroxide in methanol to yield the title compound, m.p. 179°–181° C.

EXAMPLE 22

4-(3-(4-Acetyl-3-hydroxy-2-propylphenoxy)propylthio)-3-fluoro-gamma-oxobenzenebutanoic acid-S-oxide The ester prepared according to the procedure of Example 10 was treated as in Example 21 to give, after saponification, the title compound, m.p. 135°–136° C.

EXAMPLE 23

4-(3-(4-Acetyl-3-hydroxy-2-propylphenoxy)-propylthio)-2-fluoro-gamma-oxobenzenebutanoic acid-S-oxide The ester prepared according to the procedure of Example 11 was treated as in Example 21 to give, after saponification, the title compound, m.p. 168°–169° C.

EXAMPLE 24

4-(3-(4-Acetyl-3-hydroxy-2-propylphenoxy)-2-hydroxypropylthio)-2-fluoro-gamma-oxobenzenebutanoic acid-S-oxide The ester prepared according to the to give, after saponification, the title compound, m.p. 69°–72° C.

EXAMPLE 25

4-(3-(4-Acetyl-3-hydroxy-2-propylphenoxy)propylsulfonyl)-2-fluoro-gamma-oxobenzenebutanoic acid The ester prepared according to the procedure of Example 11 dissolved in 50 mL CH was treated at room temperature with 2.5 equivalents of m-chloroperbenzoic acid for 2 hours. The reaction mixture was purified by chromatography on silica gel to yield the methyl ester of the title compound, that then was saponified by stirring with NaOH in methanol to yield the title compound, m.p. 116°–118°.

4-(3-(4-Acetyl-3-hydroxy-2-propylphenoxy)-2-hydroxypropylsulfonyl)-2-fluoro-gamma-oxobenzenebutanoic acid The ester prepared according to the procedure of Example 2 was treated as in Example 25 to give, after saponification, the title compound, m.p. 80°-85° (decomp).

EXAMPLE 27

4-(3-(4-Acetyl-3-hydroxy-2-propylphenoxy)propylsulfonyl)-3-fluoro-gamma-oxobenzenebutanoic acid The ester prepared according to the Procedure of Example 10 was treated as in Example 25 to give, after saponification, the title compound, m.p. 154°-156° C.

EXAMPLE 28

4-(3-(4-Acetyl-3-hydroxy-2-propylphenoxy)-2-hydroxypropylsulfonyl)-3-fluoro-gamma-oxobenzenebutanoic acid The ester prepared according to the procedure of Example 3 was treated as in Example 25 to give, after saponification, the title compound, m.p. 96°-99° resolidifies, 105°-108°.

EXAMPLE 29

4-(3-(4-Acetyl-3-hydroxy-2-propylphenoxy)propylsulfonyl)-gamma-oxobenzenebutanoic acid The ester prepared according to the procedure of Example 6 was treated as in Example 25 to give, after saponification, the title compound,
Analysis, calculated: C, 60.48; H, 5.92; S, 6.72. Observed: C, 60.51; H, 5.90; S, 6.48.

EXAMPLE 30

4-(3-(4-Acetyl-3-hydroxy-2-propylphenoxy)-2-hydroxypropylsulfonyl)-gamma-oxobenzenebutanoic acid The ester prepared according to the procedure of Example 1 was treated a in Example 25 to give, after saponification, the title compound.
Analysis, calculated: C, 59.27; H, 5.97; S, 6.33. Observed: C, 59.22; H, 6.13; S, 6.02.

EXAMPLE 31

4-(3-(4-Acetyl-3-hydroxy-2-propylphenoxy)propoxy)-3-chloro-gamma-oxobenzenebutanoic acid By following the procedure of Example 12 but substituting in Step A, 2-chlorophenol for 2-fluorophenol, the title compound is obtained, m.p. 167 5°-169.5°

EXAMPLE 32

4-(3-(4-Acetyl-3-hydroxy-2-propylphenoxy)-2-hydroxypropoxy)-3-fluoro-gamma-oxobenzenebutanoic acid, sodium salt, monohydrate Following the procedure of Step F of Example 1 but substituting an equivalent amount of 2-hydroxy-3-propyl-4-(3-bromopropyloxy)acetophenone for 2-hydroxy-3-propyl-4-(2,3-epoxypropoxy)acetophenone and substituting the product from Step A of Example 12 for 4-mercapto-gamma-oxobenzenebutanoic acid, methyl ester, the corresponding free acid of the title compound was isolated. It was converted to the sodium salt by treating with 1 equivalent of NaOH.
Analysis, calculated: C, 57.42; H, 5.81; F, 3.78. Observed: C, 57.49; H, 5.78; F, 4.19.

EXAMPLE 33

4-(3-(4-Acetyl-3-hydroxy-2-propylphenoxy)propoxy)-alpha,alpha-dimethyl-gamma-oxobenzene-butanoic acid A: Preparation of 3,4-dehydro-2,2-dimethyl-4-(4-methoxyphenyl)-gamma-butyrolactone To a stirring suspension of KH (16 mmole) in THF (50 ml) was added a solution of 4-methoxy-gamma-oxobenzenebutanoic acid (8 mmole) prepared as in Step A of Example 1 in THF (10 ml) at room temperature. The mixture was stirred at room temperature for 2 hours. Methyl iodide (32 mmole) was added and the resulting reaction mixture stirred at room temperature for 16 hours. Cold, dilute HCl solution was added and the resulting mixture extracted with ethyl acetate. The organic layer was washed successively with NaHCO$_3$ solution, brine, dried and evaporated.

The resulting oil was chromatographed on silica gel to give 3,4-dehydro-2,2-dimethyl-4-(4-methoxyphenyl)-gamma-butyrolactone.

B: Preparation of methyl 4-methoxy-alpha,alpha-dimethyl-gamma-oxobenzenebutanoate To 3,4-dehydro-2,2-dimethyl-4-(4-methoxyphenyl)-gamma-butyrolactone (1.35 mmole), prepared in Step A of this Example, in methanol (8 ml) was added 2.7 mmole of sodium methoxide. The reaction was stirred at room temperature for 1.5 hour. Cold dilute hydrochloric acid was then added, the methanol evaporated to dryness and the resulting aqueous layer extracted with ethyl acetate. The organic layer was then washed with brine and dried over MgSO$_4$. Evaporation of the volatiles gave a quantitive yield of the title compound.

C: Preparation of 4-(3-(4-Acetyl-3-hydroxy-2-propylphenoxy)propoxy)-alpha,alpha-dimethyl-gamma-oxobenzenebutanoic acid Following the procedure of Step B of Example 1 but substituting the product from Step B of this example for 4-methoxy-gamma-oxobenzenebutanoic acid there was obtained 4-hydroxy-alpha,alpha-dimethyl-gamma-oxobenzenebutanoic acid, methyl ester.

This ester was reacted according to the Procedure of Example 6 to yield the title compound.
Analysis, calculated: C, 68.40; H, 7.07. Observed: C, 68.54; H, 7.06.

EXAMPLE 34

4-(3-(4-Acetyl-3-hydroxy-2-propylphenoxy)propoxy)-beta-methyl-gamma-oxobenzenebutanoic acid The title compound was prepared by following the procedure of Step C of Example 33 but substituting the methyl 4-methoxy-beta-methyl-gamma-oxobenzenebutanoate (prepared as described in Step A of Example 33) for the product of Step B of Example 33.
Analysis, calculated: C, 67.86; H, 6.83. Observed: C, 67.94, H, 6.87.

EXAMPLE 35

4-(3-(4-Acetyl-3-hydroxy-2-propylphenoxy)-2-methylidenylpropoxy-gammaoxobenzenebutanoic acid A: Preparation of 2-Hydroxy-3-propyl-4-(3-chloro-2-methylidenylpropoxy)acetophenone To a solution of 2,4-dihydroxy-3-propylacetophenone, 30 g, in acetone, 600 ml, were added K$_2$CO$_3$, 64 g, and 3-chloro-2-chloromethyl-1-propene, 54 ml. The heterogeneous purple mixture was stirred at reflux overnight. The reaction mixture was filtered, the solids were washed with acetone and the filtrate was evaporated to a red oil that was chromatographed on silica gel to yield the title compound, mp 50°-52° C. as a white solid B: Preparation of 4-(3-(4-acetyl-3-hydroxy-2-propylphenoxy)-2-methylidenylpropoxy)-gamma-oxobenzenebutanoic acid Following the procedure of Step F of Example 1, but substituting the title compound of Step A of this example for 2-hydroxy-3-propyl-4-(2,3-epoxy-propoxy)acetophenone and substituting 4-hydroxy-gamma-oxobenzenebutanoic acid, methyl ester for 4-mercapto-gamma-oxobenzenebutanoic acid, methyl ester, the title compound was obtained, mp 136°-137° C.

Analysis, calculated: C, 68.17; H, 6.41. Observed: C, 68.10; H, 6.40.

EXAMPLE 36

4-(3-(4-acetyl-3-hydroxy-2-propylphenoxy)-2-methylpropoxy)-gamma-oxobenzenebutanoic acid A: Preparation of 2-Hydroxy-3-propyl-4-(2-methyl-3-chloro-propoxy)acetophenone Following the procedure of Step A of Example but substituting 2-methyl-1,3-dichloropropane for -chloro-2-chloromethyl-1-propene, the title compound was obtained.

B: Preparation of 4-(3-(4-Acetyl-3-hydroxy-2-propyl-phenoxy)-2-methylpropoxy)-gamma-oxobenzenebutanoic acid Following the procedure of Step B of Example 35, but substituting 2-hydroxy-3-propyl-4-(2-methyl-3-chloro-propoxy)acetophenone for 2-hydroxy-3-propyl-4-(-3-chloro-2-methylidenylpropoxy)acetophenone, the title compound was obtained.

Analysis, calculated: C, 67.86; H, 6.83. Observed: C, 67.62; H, 6.85.

EXAMPLE 37

4-(3-(4-acetyl-3-hydroxy-2-propylphenoxy)-2-methylidenepropoxy)-gamma-oxo-benzenebutanoic acid A: Preparation of 2-hydroxy-3-propyl-4(3-chloro-2-methylidenepropoxy)acetophenone 2,4-Dihydroxy-3-propyl-acetophenone (30 g, 15.5 mmole) was refluxed with 3-chloro-2-chloromethyl-1-propene (54 ml, 464 mmole) in 600 ml acetone for 14 hours in the presence of 3.0 equivalents of K$_2$CO$_3$. The product was purified by chromatography on silica gel using hexane/EtOAc (10:1-10:5) as eluent. The title compound was obtained as a white solid, m.p. 50°-52°.

B: Preparation of methyl 4-(3-(4-acetyl-3-hydroxy-2-propylphenoxy)-2-methylidenepropoxy)-gamma-oxo-benzenebutanoate To a stirred mixture of the compound from Step A (6.22 g, 22.0 mmole) in methylethyl ketone (110 ml) was added the compound of Example 1, Step B (5.54 g, 26.6 mmole) and 3.0 equivalents of K$_2$CO$_3$. The mixture was heated at reflux for 30 hours. The reaction mixture was cooled to room temperature, filtered, washed with acetone and evaporated to dryness. The residue was dissolved in methylene chloride, washed with 0.1N NaOH, and evaporated to an oil. The oil was purified by HPLC using hexane: EtOAc (10:4) to yield the title compound as a white solid, m.p. 89°-90°.

Analysis, calculated: C, 68.70; H, 6.65. Observed: C, 68.68; H, 6.70.

C: 4-(3-(4-acetyl-3-hydroxy-2-propylphenoxy)-2-methylidenepropoxy)-gamma-oxo-benzenebutanoic acid To a stirred solution of the compound from Step B (550 mg, 1.21 mmole) in THF (15 ml) was added 3 ml of 1N NaOH. The mixture was stirred at room temperature for 1.5 hours. The reaction mixture was diluted with H$_2$O (50 ml) and acidified with concentrated HCl to pH=5. A white solid formed which was extracted with methylene chloride (2×). The combined organic extracts were washed with brine, dried (MgSO$_4$) and concentrated in vacuo to yield the title compound as a white solid, m.p. 136°-137°.

Analysis, calculated: C, 68.17; H, 6.41. Observed: C, 68.10; H, 6.40.

EXAMPLE 38

4-(3-(4-acetyl-3-hydroxy-2-propylphenoxy)-2-methylidenepropylthio)-gamma-oxo-benzenebutanoic acid Following the procedure of Example 37, Steps B and C but substituting an equivalent amount of the compound Of Example 1, Step E (for the compound of Example 1, Step B), in Step B of Example 37, the title compound m p 123°-125° was obtained following hydrolysis of its corresponding methyl ester.

Analysis, calculated: C, 65.77; H, 6.18; S, 7.02. Observed: C, 65.74; H, 6.23; S, 7.23.

EXAMPLE 39

4-(3-(4-acetyl-3-hydroxy-2-propylphenoxy)-2-methylidenepropoxy)-3-fluoro-gamma-oxoben-zenebutanoic acid Following the procedure of Example 37, Steps B and C, but substituting an equivalent amount of the compound of Example 12, Step A, (for the compound of Example 1, Step B) in Step B of Example 37, the title compound was obtained, m.p. 132°-134°.

Analysis, calculated: C, 65.49; H, 5.94. Observed: C, 65.48; H, 5.99.

EXAMPLE 40

4-(3-(4-acetyl-3-hydroxy-2-propyl-phenoxy)propylthio)gamma-oxobenzenebutyronitrile A: Preparation of 4-methylthio-gamma-oxobenzenebutyronitrile A solution of 4-methylthiobenzaldehyde (15.2 g, 100 mmole) in dry DMF (50 ml) was added over 10 minutes to a solution of sodium cyanide (2.45 g, 50 mmole) in DMF (50 ml) at 35° C. After 5 minutes, acrylonitrile (4.0 g, 75 mmole) in DMF (100 ml) was added dropwise over 20 minutes. The reaction mixture stirred at 35° for 3 hours. The reaction mixture was cooled to room temperature, diluted with water (400 ml), extracted with chloroform, washed with 0.01N H , 5% NaHCO$_3$ and water, dried, and evaporated to a solid which was crystallized from ethyl acetate and hexane to yield the title compound, m.p. 122°-124°.

B: Preparation of 4-methylthio-gamma-oxobenzenebutyronitrile-S-oxide

The compound of Step A above (205 mg, 1.0 mmole) was dissolved in chloroform (1 ml) and cooled to 0°. m-Chloroperbenzoic acid (200 mg, 1.1 mmole) in chloroform (1 ml) was added to the cooled solution, and the reaction mixture warmed to room temperature over 30 minutes. Calcium hydroxide (210 mg) was added and the reaction stirred 15 minutes. The solution was filtered and evaporated to dryness to yield the title compound which was used directly in the following step.

C: Preparation of 4-trifluoroacetyloxymethylthio-gamma-oxo-benzenebutyronitrile

The compound of Step B above, (300 mg) was dissolved in 2.0 ml trifluoroacetic anhydride. The reaction mixture was heated at reflux for 30 minutes, cooled to room temperature, and evaporated to dryness. The title compound crystallized on standing Mass spectrum m/e 317 (M+).

D: Preparation of 4-mercapto-gamma-oxobenzenebutyronitrile

The compound of Step C above, (75 mg, 0.24 mmole) was dissolved in methanol (5 ml). To this solution was added 1N Na (0.5 ml, 0.5 mmole) and the mixture was stirred at room temperature for 30 minutes. 6N HCl (0.2 ml) was added and the reaction mixture was extracted with chloroform, washed with brine, dried and evaporated to dryness to yield the title compound. Mass spectrum m/e 191 (M+).

E: 4-(3-(4-acetyl-3-hydroxy-2-propyl-phenoxy) propylthio)-gamma-oxobenzenebutyronitrile The compound of Step D above, (2.4 g, 12.5 mmole), 2-hydroxy-3-propyl-4-(3-bromopropyloxy)acetophenone (2.92 g) and K (4.0 g) were dissolved in methylethyl ketone (50 ml). The reaction mixture was heated at reflux for 90 minutes. The reaction mixture was poured into water, extracted with chloroform, washed with brine, dried and evaporated to yield the title compound. Recrystallization from ether:hexane (1:1) afforded the title compound as needles, m.p., 94°-95°.

Analysis, calculated: C, 67.74; H, 6.39; S, 3.29. Observed: C, 67.78; H, 6.65; s, 3.25.

EXAMPLE 41

5-(3(4-(3-(4-acetyl-3-hydroxy-2-propylphenoxy) propylthio)phenyl)-3-oxopropyl)-1H-tetrazole The nitrile from Example 40, Step E, (1.0 g, 2.35 mmole) and tri-n-butyltin azide (1.0 g, 3.0 mmole) in dry THF (20 ml) were stirred at 70° for 48 hours, and then heated at reflux for 24 hours. The reaction mixture was cooled to room temperature, diluted with ether (20 ml) and concentrated HCl was added. After 1 hour, the solution was filtered, the solid was washed with ether and dried to yield the title compound.

Analysis, calculated: C, 61.52; H, 6.02; N, 11.96; S, 6.84. Observed: C, 61.60; H, 6.13; N, 11.91; S, 6.99.

EXAMPLE 42

4-(3-(4-acetyl-3-hydroxy-2-propylphenoxy)propylsulfonyl)-gamma-oxobenzenebutyronitrile The nitrile from Example 40, Step E, (680 mg, 1.6 mmole) and m-chloroperbenzoic acid (85%, 760 mg, 3.75 mmole) were stirred at 0° for two hours in 20 ml of $CH_2Cl_2$. Calcium hydroxide (400 mg) was added to the reaction mixture which was stirred for 1.5 hours. The reaction mixture was filtered and evaporated to dryness, affording the title compound, mp 143°-144°.

Analysis, calculated: C, 63.00; H, 5.95; N, 3.06; S, 7.01. Observed: C, 63.09; H, 5.95; N, 3.38; S, 7.02.

EXAMPLE 43

5-(3-(4-(3-(4-acetyl-3-hydroxy-2-propylphenoxy) propylsulfonylphenyl)-3-oxopropyl)-1H-tetrazole Following the procedure of Example 41, but substituting an equivalent amount of the nitrile from Example 42 for the nitrile from Example 40, Step E, there was obtained the title compound; m.p. 175°-177°.

Analysis, calculated: C, 57.59; H, 5.64; N, 11.19; S, 6.41. Observed: C, 57.64; H, 5.74; N, 11.18; S, 6.61.

EXAMPLE 44

4-(3-(4-acetyl-3-hydroxy-2-propyl-phenoxy)propylsulfonyl)-epsilon-oxobenzenehexanoic acid A: Preparation of methyl 4-(3-bromopropylthio)epsilon-oxobenzenehexanoate Adipoylchloride monomethylester (5.95 g, 33.3 mmole) in dichloroethane (15 ml) was added dropwise to a suspension of aluminum chloride 4.5 g, 33.7 mmole) in dichloroethane (50 ml). The reaction mixture was stirred at room temperature for 20 minutes 3-Bromopropylthiobenzene (7.0 g, 30.0 mmole) in dichloroethane (15 ml) was added dropwise to the stirred suspension over 30 minutes. Additional aluminum chloride (4.0 g ) was added to complete the reaction After 30 minutes the reaction mixture was poured into ice water (500 ml) and extracted with chloroform. The organic layer was washed with brine, dried and concentrated. The residue was crystallized from ether hexanes to yield the title compound.

NMR ($CDCl_3$) :1.73 (4H, m), 2.26 (4H, m), 2.93 (2H, m), 3.15 (2H, m), 3.50 (2H, m), 3.63 (3H, s), 7.32 (2H, d), 7.90 (2H, d).

B: Preparation of methyl 4-(3-(4-acetyl-3-hydroxy-2-propylphenoxy)-propylthio)-epsilon-oxo-benzenehexanoate The compound of Step A above, (2.0 g, 5.36 mmoles), 2,4-dihydroxy-3-propylacetophenone (2.08 g, 10.72 mmole) and potassium carbonate (3.0 g, 21.44 mmole) were stirred in methyl ethyl ketone (100 ml) and heated at reflux for three hours. The reaction mixture was filtered and concentrated in vacuo. The residue was dissolved in ether-methanol and extracted with 1N NaOH (3×50 ml). The organics were dried and concentrated in vacuo. The residue was triturated with methanol, filtered and dried, to yield the title compound. NMR ($CDCl_3$): 0.94 (3H, m), 1.73 (6H, m), 2.28 (6H, m), 2.95 (2H, m), 3.22 (2H, m), 3.66 (3H, s), 4.17 (2H, m), 6.42 (1H, d), 7.40 (2M, d), 7.61 (1H, d), 7.90 (2H, d), 12.73 (1H, s).

C: Preparation of methyl 4-(3-(4-acetyl-3-hydroxy-2-propylphenoxy)-propylsulfonyl)-epsilon-oxo-benzenehexanoate The compound of Step B above, (1.0 g, 2.05 mmoles) was dissolved in dry methylene chloride (25 ml) to which was added one equivalent of m-chloroperbenzoic acid in methylene chloride (10 ml). After 1 hour stirring at room temperature, additional m-CPBA (450 mg) was added. The reaction was complete in two hours Calcium hydroxide (1.0 g) was added and the reaction mixture was stirred for 10 minutes. The mixture was filtered and the filtrate concentrated. The residue was purified by chromatography to yield the title compound. NMR ($CDCl_3$): 0.90 (3H, m), 1.50 (2H, m), 1.74 (4H, m), 2.33 (6H, m), 2.55 (3H, s), 3.03 (2H, m), 3.37 (2H, m), 3.68 (3H, s), 4.12 (2H, m), 6.39 (2H, d), 7.60 (2H, d), 8.12 (4H, m), 12.73 (1H, s).

D: Preparation of 4-(3-(4-acetyl-3-hydroxy-2-propylphenoxy)propylsulfonyl)-epsilon-oxobenzenehexanoic acid The compound of Step C above, (800 mg. 1.54 mmoles, 1N NaOH (3.2 ml), water (3.2 ml) and THF (10 ml) were stirred at room temperature for three hours. The THF layer was removed and the aqueous portion diluted with water and extracted with ether. The aqueous portion was acidified with concentrated HCl. A solid precipitate formed which was extracted into ether, dried and concentrated. Trituration of the residue with ether-methanol afforded the title compound; mp 138°-140°.

EXAMPLE 45

4(3-(4-acetyl-3-hydroxy-2-propylphenoxy)propylthio-)epsilon-oxobenzenehexanoic acid The compound of Example 44, Step B (1.0 g, 2.055 mmole) was dissolved in THF (10 ml). To this solution was added 1N NaOH (4.1 ml). The reaction mixture was stirred at room temperature for two hours. Additional 1N NaOH was added and stirring continued for two hours. The THF solution was removed and the aqueous portion diluted with water and extracted with ether. The aqueous layer was acidified with concentrated HCl, extracted with chloroform, dried and evaporated. Trituration of the residue with ether/methanol afforded the title compound; m.p. 130°-132°.

EXAMPLE 46

4-(3-(4-acetyl-3-hydroxy-2-propylphenoxy)-propylthio)delta-oxo-benzenebutanol

A: Preparation of 4(3-bromopropylthio)-gamma-oxobenzenebutanoic acid

A mixture of the product of Example 1, Step E (5 g), 1,3-dibromopropane (20 g) and $K_2CO_3$ (10 g) was refluxed in methylethylketone (100 ml) for 20 hours. The cooled reaction mixture was filtered, the solvent evaporated and the residue purified by chromatography over silica gel. The resulting ester of the title compound was hydrolyzed by dissolving in a mixture of 25 ml of methanol and 15 ml of 1N NaOH and stirring at 25° C. for 4 hours. The reaction mixture was diluted with 100 ml of water, acidified with citric acid and extracted with 2×100 ml of EtOAc. The combined organic layers were washed with brine, dried over $Na_2SO_4$ and evaporated to yield the title compound which was sufficiently pure for use in the next step, m.p. 91°-94°.

B: Preparation of 4(3-bromopropylthio)-delta-oxobenzenebutanol (A) and 4-(3-bromopropylthio)delta-hydroxy-benzenebutanol (B)

4-(3-Bromopropylthio)-gamma-oxobenzenebutanoic acid (3.4 g, 10.3 mmoles) was dissolved in THF (25 ml) and cooled to −15°. Borane-THF complex (10 ml, 10.4 mmoles) was added dropwise over one hour. The solution warmed to room temperature with stirring over 12 hours. The reaction mixture was diluted with methanol, stirred for 30 minutes and evaporated in vacuo. The residue was treated with an excess of diazomethane and following workup and separation by HPLC the title compounds were obtained.

C: Preparation of 4-(3-(4-acetyl-3-hydroxy-2-propylphenoxy)-propylthio)-delta-oxo-benzenebutanol The compound A of Step B above (96 mg, 0.29 mmoles), 2,4-dihydroxy-3-propylacetophenone (78 mg, 0.4 mmole) and potassium carbonate (270 mg, 2.0 mmoles) were refluxed in methyl ethyl ketone (3 ml) for twelve hours. The reaction mixture was filtered and purified by chromatography to yield the title compound; m.p. 73°-75°.

Analysis, calculated: C, 66.95; H, 7.02; S, 7.45. Observed: C, 67.00; H, 7.11; S, 7.22.

EXAMPLE 47

4(3-(4-acetyl-3hydroxy-2-propylphenoxy)propylsulfonyl)-delta-oxobenzenebutanol

The compound of Example 46. Step B (330 mg, 0.767 mmoles) was dissolved in chloroform and cooled to 0°. m-Chloroperbenzoic acid (328 mg, 1.57 mmoles) was added and the reaction stirred for one hour. Calcium hydroxide (195 mg) was added and the reaction stirred for 90 minutes at room temperature. The mixture was filtered and the filtrate evaporated to dryness. The residue crystallized from ethyl acetatehexane to yield the title compound; m.p. 99°-100°.

Analysis, calculated: C, 62.32; H, 6.54; S, 6.93. Observed: C, 62.23; H, 6.50; S, 6.68.

EXAMPLE 48

4-(3-(4-acetyl-3-hydroxy-2-propylphenoxy)propylthio-beta,epsilon-dioxobenzenepentanol A: Preparation of 4-(3-(4-acetyl-3-hydroxy-3-propylphenoxy)propylthio-alpha-isobutylyloxycarbonyloxy-alpha.delta-dioxobenzenebutane Isobutylchloroformate (260 μl, 2.0 mmoles) was added to 10 ml methylene chloride and cooled to −30°. The compound of Example 6, (890 mg, 2.0 mmoles) was dissolved in a mixture of methylene chloride (6 ml) and triethylamine (280 μl) and added dropwise to the −30° solution. The reaction mixture was maintained at −30° for 30 minutes, then held at 0° for 30 minutes. The reaction mixture was concentrated in vacuo to yield the title compound which was used without further purification in the next step.

B: Preparation of 4-(3-(4-acetyl-3-hydroxy-2-propylphenoxy)propylthio-alpha-diazomethyl-alpha,delta-dioxobenzenebutane The crude compound from Step A above (1.1 g) was dissolved in toluene (20 ml) and cooled to 0°. An excess amount of diazomethane was added to the solution and the reaction mixture was stirred for twelve hours. The reaction mixture was purged with air, filtered and concentrated in vacuo to yield the title compound which was used in the next step without further purification.

C: Preparation of 4-(3-(4-acetyl-3-hydroxy-2-propylphenoxy)propylthio-beta-epsilon-dioxo-benzeneoentanol The crude compound from Step B above (800 mg) was dissolved in chloroform (20 ml) to which was added trifluoroacetic acid (excess) The reaction mixture stirred at room temperature for two hours, was filtered, and concentrated in vacuo. The residue was purified by column chromatography to yield the title compound, m.p. 87°-89°.

EXAMPLE 49

4-(3-(4-acetyl-3-acetoxy-2-propylphenoxy)propylthio)-gamma-oxo-benzenebutanoic acid To a suspension of the compound of Example 6, (1.2 g, 2.7 mmoles) and dihydropyran (0.8 ml, 4.4 mmoles) in methylene chloride (20 ml) was added p-toluenesulfonic acid monohydrate (5 mg) The reaction mixture was stirred at room temperature for two hours. The solution was cooled to 0° and triethylamine (6 ml), 4-dimethylaminopyridine (DMAP) (15 mg) and acetic anhydride (5 ml) were added. The resulting solution stirred at room temperature for two hours. The solution was washed with 5% NaHCO3 (2×), water, 1N HCl and concentrated in vacuo. The residue was dissolved in THF (6 ml) and stirred with 1N HCl (1 ml) at room temperature for one hour. Dichloromethane (50 ml) and water (50 ml) were added to the solution and the organic layer was collected, washed with brine (4×) dried (Na2SO4) and concentrated in vacuo. The crystalline residue was washed with hexane and recrystallized to afford the title compound, m.p. 121°-123°.

Analysis, calculated: C, 64.18; H, 6.21; S, 6.59. Observed: C, 64.20; H, 6.30; S, 6.62.

EXAMPLE 50

4-(3-(4-acetyl-3-acetoxy-2-propylphenoxy)-propylsulfontl)-gamma-oxobenzenebutanoic acid Following the procedure of Example 49, but substituting an equivalent amount of the compound of Example 29, for the compound of Example 6, was obtained the title compound, m.p. 128°-131°.

Analysis, calculated: C, 60.22; H, 5.83; S, 6.18. Observed: C, 60.30; H, 5.95; S, 6.29.

EXAMPLE 51

4-(3-(4-acetyl-3-hydroxy-2-propylphenoxy)-propylsulfonyl-gamma-oxobenzenebutyramide A solution of the compound of Example 29, (1 g, 2.12 mmoles) and triethylamine (310 μl, 2.2 mmoles) in methylene chloride (5 ml) was cooled to −30°. Isobutylchloroformate (286 μl, 2.2 mmoles) was added to the −30° solution over ten minutes. The reaction mixture was warmed to 0° and stirred for 30 minutes. Anhydrous ammonia was bubbled into the cold solution for 10 minutes. The reaction mixture warmed to room temperature and stirred for 15 minutes. The solution was filtered and the solids washed with chloroform, to yield the title compound, m.p. 198°-199° (dec.).

Analysis, calculated: C, 60.62; H, 6.15; N, 2.94; S, 6.74. Observed: C, 60.53; H, 6.32; N, 2.98; S, 6.84.

EXAMPLE 52

N-methylsulfonyl 4-(3-(4-acetyl-3-hydroxy-2-propylphenoxy)propylthio-gamma-oxobenzenebutyramide A solution of the compound of Example 6, (1.32 g, 3.0 mmoles) and triethylamine (0.42 ml, 3.0 mmoles) in methylene chloride (6 ml) was added to a solution of isobutylchloroformate (0.39 ml, 3.0 mmoles) in methylene chloride (6 ml) at −30°. The mixture was stirred at 0° for thirty minutes, then triethylamine (1.26 ml, 9.7 mmoles) and methanesulfonamide (0.60 g, 9.5 mmoles) were added and the reaction stirred at room temperature for 24 hours. The mixture was poured into water, acidified with 1N HCl, and extracted with methylene chloride (3×). The combined organic extracts were washed with brine, dried (Na2SO4) and concentrated in vacuo. The residue was washed with ether and recrystallized to afford the title compound as needles, m.p. 148°-150°.

Analysis, calculated: C, 57.56; H, 5.99; N, 2.69; S, 12.29. Observed: C, 57.89; H, 6.31; N, 2.90; S, 12.29.

EXAMPLE 53

5(4-(3-(4-acetyl-3-hydroxy-2-propylphenoxy)propylsulfonyl)phenyl)-2(3H)-furanone The compound of Example 29, (2.0 g, 4.197 mmoles) was suspended in chloroform (120 mls) to which was added 1,1-dichloromethylmethyl ether (10 ml). The reaction mixture was heated at 40° for 48 hours, and concentrated in vacuo. The residue was recrystallized to afford the title compound, m.p. 135°-136°.

Analysis, calculated: C, 62.87; H, 5.72; S, 6.99. Observed: C, 62.70; H, 5.75; S, 7.11.

PRODRUG EXAMPLES

The following Table lists various prodrug derivatives (Formula XV) of the compounds of the present invention. The processes for preparing these compounds are discussed supra.

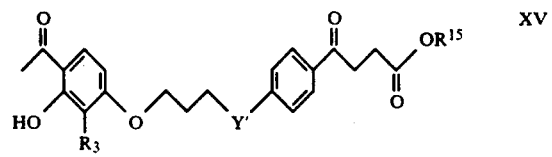

XV

R3 in Formula XV is n-propyl.

TABLE I

| EXAMPLE NO. | L-Number | Y¹ | OR¹⁵ |
|---|---|---|---|
| 54 | L-649,874-00M01 | S | −O−CH2−O−C(O)−CMe3 |
| 55 | L-649,888-00P01 | SO2 | −O−CH2−O−C(O)−CMe3 |
| 56 | — | S | −O−CHMe−O−C(O)−CMe3 |
| 57 | L-649,948-00E01 | SO2 | −O−CHMe−O−C(O)−CMe3 |
| 58 | L-649,875-00W01 | S | −O−CH2−C(Me)=CH−O−C(O)−O (cyclic carbonate) |
| 59 | L-649,893-00N01 | SO2 | −O−CH2−C(Me)=CH−O−C(O)−O (cyclic carbonate) |

TABLE I-continued

| EX-AMPLE NO. | L-Number | Y¹ | OR¹⁵ |
|---|---|---|---|
| 60 | L-649,876-00E01 | S | -O-CH₂-N(C(=O)-)(C(=O)-)N-Me (imidazolidine-2,4-dione methoxy) |
| 61 | L-649,877-00N01 | SO₂ | -O-CH₂-N(C(=O)-)(C(=O)-)N-Me |
| 62 | — | S | -O-CH(Me)-N(C(=O)-)(C(=O)-)N-Me |
| 63 | L-649,951-00L01 | SO₂ | -O-CH(Me)-N(C(=O)-)(C(=O)-)N-Me |
| 64 | L-649,930-00T01 | S | -O-CH₂-N(pyrrolidinone) |
| 65 | L-649,931-00B01 | SO₂ | -O-CH₂-N(pyrrolidinone) |
| 66 | L-649,932-00K01 | S | -O-CH(Me)-N(succinimide) |
| 67 | L-649,933-00001 | SO₂ | -O-CH(Me)-N(succinimide) |
| 68 | — | S | -O-CH₂-N(succinimide) |
| 69 | L-649,952-00V01 | SO₂ | -O-CH₂-N(succinimide) |

EXAMPLE 70

4(3(4-Acetyl-3-hydroxy-2-propylphenoxy)propyloxy)-gamma-oxo-beta,beta-dimethylbenzenebutanoic acid A: Preparation of Methyl 4-methoxy-gamma-oxo-beta-methylbenzenebutanoate A solution of diisopropylamine (5.1 ml) in anhydrous THF (90 ml) at 0° C. is treated under N2 atmosphere with n-butyllithium (1.6 M, 22 ml) for 20 minutes. The mixture was cooled to −78° C., and a solution of 1(4-methoxyphenyl)-1-oxopropane (5 g) in anhydrous THF (40 ml) is added. The mixture was stirred 30 minutes at −78° C., then methyl bromoacetate (3.05 ml) was added dropwise and then mixture was warmed to ambient temperature over 2 hours. After stirring 18 hours at room temperature the mixture was Poured onto ice, water and conc. HCl (3 ml) was added and the solution was extracted with dichloromethane. The organic extracts were washed with brine, dried over $N_2SO_4$ and concentrated to an oil which was purified by chromatography on silica gel to provide the title compound as an oil.

NMR ($CDCl_3$): 1.2 (3H, m), 2.2–3.1 (2H, m), 3.6 (3H, s), 3.85 (3H, S), 3.7–4.0 (1H, m), 6.9 (2H, d), 8.0 (2H, d).

B: Preparation of Methyl 4-methoxy-gamma-oxo-beta, beta-dimethylbenzenebutanoate The product from Step A,. (3.05 g) was stirred in methanol (30 ml) and 1N NaOH (15 ml) at ambient temperature for 1 hour. The mixture was diluted with brine (50 ml), washed with ethyl acetate, acidified with conc. HCl and extracted with ethyl acetate (2×50 ml). The second organic extract was washed with brine, dried ($Na_2SO_4$) and reduced to dryness. The resulting oil was dissolved in anhydrous THF (20 ml) and added to a suspension of potassium hydride (1.56 g) in THF (20 ml) under nitrogen at −40° C. DMSO (50 μl) was added and the mixture was warmed to 0° C. for ½ hr., cooled to −40° and then treated with methyl iodide (3.7 ml). After ½ hour at −40° C., the mixture was stirred at ambient temperature for 18 hours, then poured onto an excess of ice-conc HCl mixture and was extracted with ethyl acetate. The organic extract was washed with brine, dried ($Na_2SO_4$) and reduced to dryness. The resulting oil was dissolved in anhydrous methanol, saturated with HCl gas, and after 1 hour reduced to dryness to yield an oil which was Purified by chromatography on silica gel to yield the title compound as an oil. NMR ($CDCl_3$): 1.46 (6H, s), 2.78 (2H, s), 3.60 (3H, s), 3.82 (3H, s), 6.88 (2H, d), 7.80 (2H, d).

C: Preparation of Methyl 4-hydroxy-gamma-oxo-beta, beta-dimethylbenzenebutanoate The product from Step B, (1.72 g) in $CH_2Cl_2$ (10 ml) at −78° C., was treated with boron tribromide (22 ml of a 1M solution in $CH_2Cl_2$). After ½ hour at −78° C. the mixture was stirred at ambient temperature for 18 hours. The mixture was cooled to 0° C. treated with methanol (5 ml) then washed with water, brine, dried over Na$_2$SO$_4$ and reduced to dryness to yield an oil which was purified by chromatography on silica gel to provide the title compound as an oil.

NMR (CDCl$_3$): 1.45 (6H, s), 2.78 (2H, s), 3.60 (3H, s), 6.80 (2H, d), 7.67 (2H, d).

D. Preparation of Methyl 4-(3-(4-acetyl-3-hydroxy-2-propylphenoxy)propyloxy)-gamma-oxo-beta,beta-dimethylbenzenebutanoate A mixture of the product from Step C (250 mg), 4-(3-bromopropyl)-2-hydroxy-3-propylacetophenone (315 mg), and potassium carbonate (410 mg) in methyl ethyl ketone (10 ml) was refluxed under N$_2$ for 4 hours then stirred at ambient temperature for 18 hours. The mixture was filtered, washed with brine, evaporated to dryness and the resulting oil was Purified by chromatography on silica gel to provide the title compound as an oil. NMR (CDCl$_3$) 0.90 (3H, t), 1.43 (6H, s), 1.52 (2H, m), 2.30 (2H, m), 2.50 (3H, s), 2.55 (2H, m), 2.75 (2H, s), 3.57 (3H, s), 4.18 (4H, m), 6.41 (1H, d), 6.88 (2H, d), 7.53 (1H, d), 7.72 (2H, d).

E. Preparation of 4-(3-(4-acetyl-3-hydroxy-2-propylphenoxy)propyloxy)-gamma-oxo-beta,beta-dimethyl-benzebutanoic acid The ester from Step D (740 mg) in methanol (1 ml) and THF (10 ml) was treated with 1N NaOH (4 ml) at ambient temperature for 2 hours. The mixture was acidified with conc. HCl, diluted with brine, extracted with ethyl acetate and the organic extracts were washed with brine, dried (Na$_2$SO$_4$) and evaporated to dryness to yield an oil which was purified by chromatography on silica gel to yield the title compound as a viscous oil.

NMR: (CDCl$_3$): 0.89 (3H, t), 1.40 (8H, s and m), 2.30 (2H, m), 2.50 (3H, s), 2.5–2.8 (4H, m), 4.22 (4H, m), 6.47 (1H, d), 6.90 (2H, d), 7.49 (3H, m), 12.70 (1H, s).

EXAMPLE 71

D,L-Sodium 4-(3-(4-acetyl-3-hydroxy-2-propylphenoxy) propyloxy)-gamma-hydroxy-beta,beta-dimethylbenzenebutanoate A: Preparation of 4-hydroxy-gamma-hydroxy-beta,-beta-dimethylbenzenebutanoic acid gamma lactone The phenol from Example 70, Step C, (1.19 g) in dioxane (5 ml) was treated with sodium borohydride (190 mg) and the mixture was stirred 18 hours at ambient temperature. The solution was poured into 1N HCl (10 ml) and extracted with ethyl acetate. The extracts were washed with brine, dried (Na$_2$SO$_4$) and concentrated to dryness. The residue was recrystallized from chloroform-hexane to provide the title compound, m.p. 157°–158° C.

B: Preparation of 4-(3-(4-acetyl-3-hydroxy-2-propyl-phenoxy)-propoxy)-gamma-hydroxy-beta,beta-dimethylbenzebutanoic acid gamma lactone The lactone from Step A (85 mg), 4-(3-bromopropyloxy)-3-propyl-2-hydroxyacetophenone (160 mg) and potassium carbonate (210 mg) were refluxed together in methyl ethyl ketone (5 ml) under N$_2$ atmosphere for 8 hours. The mixture was cooled, diluted with ethyl acetate, washed with brine, dried (Na$_2$SO$_4$) and evaporated to an oil which was purified by chromatography on silica gel to provide the title compound as an oil, NMR (CDCl$_3$): 0.68 (3H, s), 0.90 (3H, t), 1.22 (3H, s), 1.52 (2H, m), 2.30 (2H, m), 2.47 (2H, m), 2.53 (3H, s), 2.60 (2H, m), 4.18 (4H, m), 5.08 (1H, s), 6.47 (1H, d), 6.87 (2H, d), 7.18 (2H, d), 7.60 (1H, d), 12.72 (1H, s).

C. Preparation of D,L-sodium 4-(3-(4-acetyl-3-hydroxy-2-propylphenoxy)propyloxy)-gamma-hydroxy-beta,beta-dimethylbenzenebutanoate The product from Step B (950 mg) was stirred in methanol (2 ml), THF (20 ml) and 1N NaOH (4.5 ml) for 2.5 hours. The mixture was concentrated to near dryness, taken up in water (10 ml) and applied to a column of XAD-8 resin (2×40 cm). After standing 1 hour, the column was washed with water until the effluent pH was neutral. Methanol (50 ml) was applied to the column and the effluent was concentrated to dryness and the residue was triturated with ether to provide the title compound as a powder, mp 101°–103°.

Analysis, calculated: C$_{26}$H$_{33}$O$_7$N$_2$: C, 64.99; H, 6.92. Observed: C, 65.18; H, 7.04.

EXAMPLE 72

4-(3-(4-acetyl-3-hydroxy-2-propylphenoxy)propylthio)-gamma-oxo-beta,beta-dimethylbenzenebutanoic acid A: Preparation of 1(4-methylthiophenyl)-1-propanone To a mixture of thioanisole (5.0 g) and propionyl chloride (3.9 ml) at 0° C. in dichloroethane (80 ml) was added AlCl$_3$ (6.4 g) in portions. The mixture was stirred 12 hours at ambient temperature, poured into water (200 ml) and conc. HCl (2 ml), then extracted with CH$_2$Cl$_2$. The extract was reduced to dryness to provide the title compound mp 60°–61° C. after purification by chromatography on silica gel.

B. Preparation of methyl 4-methylthio-gamma-oxo-beta-methylbenzenebutyrate

The ketone from Step A (180 mg) in THF (2 ml) was added to a solution of lithium diisopropylamide (1.1 mmole) in THF (3 ml) at −78° under N$_2$ atmosphere. After 15 minutes methyl bromoacetate (100 μl) was added and the mixture was warmed to ambient temperature and stirred 12 hours. The mixture was poured into water (15 ml) and conc. HCl (2 ml), extracted with CH$_2$Cl$_2$ and the extracts were dried (Na$_2$SO$_4$) evaporated to dryness and the residue purified by chromatography on silica gel to provide the title compound as an oil. NMR (CDCl$_3$): 1.2 (3H, d), 2.55 (3H, s), 2.3–3.1 (2H, m), 3.65 (3H, s), 3.95 (1H, m), 7.3 (2H, d), 7.95 (2H, d).

C. Preparation of 4-methylthio-gamma-oxo-beta-methylbenzenebutanoic acid

The ester from Step B (1.07 g) was saponified with 1N NaOH (5 ml) and methanol (5 ml) and THF (5 ml) to provide after acidification, extraction into CH and evaporation to dryness the title compound, mp 69°–71° C.

D. Preparation of Methyl 4-methylthio-gamma-oxo-beta, beta-dimethylbenzenebutyrate The acid from Step C (3.03 g) in THF (10 ml) was added to a suspension of KH (1.9 g) in THF (50 ml) at −40° under argon. DMSO (50 μl) was added, the mixture was stirred at −5° C. until gas evolution ceased, then recooled to −40° C. followed by addition of methyl iodide (1.8 ml). After 0.5 hour at −40° and 12 hours at ambient temperature, the mixture was diluted with water, acidified with HCl and extracted with CH$_2$Cl$_2$. The organic extracts were dried (Na$_2$SO$_4$) and evaporated to an oil which was treated with excess diazomethane in ether. After concentration the residue was purified by chromatography on silica gel to Provide the title compound.

NMR (CDCl₃): 1.40 (6H, s), 2.55 (3H, s), 2.75 (2H, s), 3.67 (3H, s), 7.23 (2H, d), 7.57 (2H, d).

E. Preparation of methyl 4-(3-(4-acetyl-3-hydroxy-2-propylphenoxy)propylthio-gamma-oxo-beta,beta-dimethylbenzenebutyrate The ester from Step D (0.71 g) was treated in CH₂Cl₂ (10 ml) at 0° C. with m-chloroperbenzoic acid (0.57 g) for 10 minutes, Ca(OH)₂ in excess was added and after 10 minutes at ambient temperature the mixture was filtered and evaporated to dryness. The residue was refluxed with trifluoroacetic anhydride (7 ml) for 20 minutes then concentrated to dryness The residue was mixed with 2-hydroxy-3-propyl-4-(3-bromopropyloxy)acetophenone (0.945 g) and K₂CO₃ (1.2 g) in methyl ethyl ketone (10 ml) and water (50 μl) and the mixture was stirred at 20° C. for 15 hours. The mixture was concentrated, partitioned between dilute HCl and CH₂Cl₂. The organic extracts were concentrated and purified by chromatography on silica gel to provide the title compound. NMR (CDCl₃) 1.40 (6H, s), 2.77 (2H, s), 7.13 (2H, d), 7.37 (2H, d), 12.75 (1H, s).

F: Preparation of 4-(3-(4-acetyl-3-hydroxy-2-propylphenoxy)propylthio)-gamma-oxo-beta,beta-dimethylbenzenebutanoic acid The ester from Step E (0.984 g) was saponified, acidified and the product purified by chromatography on silica gel to provide the title compound.

Analysis, calculated: C, 66.07; H, 6.83; S, 6.79. Observed: C, 66.14; H, 6.86; S, 6.51.

EXAMPLE 73

Sodium 4-(3-(4-acetyl-3-hydroxy-2-propylphenoxy)propylthio)-gamma-hydroxy-beta,beta-dimethylbenzenebutyrate A: Preparation of methyl 4(3-bromopropylthio)-gamma-oxo-beta,beta-dimethylbenzenebutyrate Following the procedure described in Example 72, Step E but substituting three equivalents of dibromopropane in place of 4(3-bromopropyloxy) 2-hydroxy-3-propyl acetophenone was obtained the title compound as an oil. NMR (CDCl₃): 1.40 (6H, s), 2.0–2.3 (2H, m), 2.77 (2H, s), 3.13 (2H, t), 3.50 (2H, t), 3.67 (3H, s), 7.23 (2H, d), 7.57 (2H, d).

B: Preparation of 4-(3-bromopropylthio)-gamma-hydroxy-beta,beta-dimethylbenzenebutanoic acid gamma lactone The ester from Step A (1.4 g) in methanol (10 ml) was treated at −15° C. with ceric chloride (2 mg) and NaBH₄ (100 mg) for 1 hour. The mixture was diluted with water, (100 ml) acidified with 1N HCl and extracted with CH₂Cl₂. The extracts were left for 2 days at room temperature, concentrated and purified by chromatography on silica gel to provide the title compound as an oil. NMR (CDCl₃): 0.20 (3H, s), 1.27 (3H, s), 2.0–2.3 (2H, m), 2.37 (1H, d), 2.60 (1H, d), 3.07 (2H, t), 3.50 (2H, t), 5.10 (1H, s), 7.13 (2H, d), 7.33 (2H, d).

C: Preparation of 4-(3-(4-acetyl-3-hydroxy-2-propylphenoxy)propylthio-gamma-hydroxy-beta,beta-dimethylbenzenebutanoic acid gamma lactone The lactone from Step B (0.95 g) and 2,4-dihydroxy-3-propylacetophenone (0.54 g) were placed with K₂CO₃ (1.2 g) in methyl ethyl ketone (10 ml) for 4 hours. The mixture was filtered, diluted with CH₂Cl₂, washed with water, dried (Na₂SO₄) concentrated and chromatographed on silica gel to provide the title compound as an oil. Mass spectrum m/e 456 (M⁺).

D. Preparation of Sodium 4-(3-(4-acetyl-3-hydroxy-2-propylphenoxy)propylthio-gamma-hydroxy-beta,-beta-dimethylbenzenebutyrate The lactone from Step C (0.936 g) was saponified with 1N NaOH (4 ml) THF (4 ml) and MeOH (4 ml) for 45 minutes at ambient temperature. The mixture was concentrated to near dryness and then purified on XAD-8 resin to provide the title compound as a foam.

Analysis, calculated: C, 62.88; H, 6..70; S, 6.46. Observed: C, 62.71; H, 6.81; S, 6.46.

EXAMPLE 74

Resolution of Sodium (beta S*, gamma R*)-4-(3-(4-acetyl-3-hydroxy-2-propylphenoxy)propylthio-gamma-hydroxy-beta-methylbenzenebutanoate into the (+) isomer and the (−)-isomer A: Preparation of methyl (beta S, gamma R)-4-(3-(4-acetyl-3-hydroxy-2-propylphenoxy)propylthio)gamma-(d-(alpha-methoxy)phenylacetoxy)-beta-methyl-benzenebutanoate and methyl (beta R, gamma S)-4(3-(4-acetyl-3-hydroxy-2-propylphenoxy)propylthio)-gamma-(d-(alpha-methoxy)phenylacetoxy)-beta-methylbenzenebutanoate To the lactone (360 mg) from Example 75 in THF (4 ml) and MeOH (1.5 ml) was added 1N NaOH (2 ml). After 30 minutes at room temperature the solution was evaporated and ethyl acetate (20 ml) was added. The mixture was cooled to 0° and acidified with HCl (1N). The ethyl acetate layer was separated and the aqueous layer was re-extracted with ethyl acetate. The combined organic layers were dried (Na₂SO₄) and evaporated to give crude hydroxy acid. To the crude acid in ethyl acetate was added excess CH₂N₂. The reaction mixture was stirred 10 minutes at room temperature and evaporated. To the residue was added THF (10 ml), Et₃N (0.6 ml), DCC (500 mg), DMAP (5 mg) and d-α-methoxy mandelic acid (500 mg) The reaction mixture was stirred at room temperature 2 hours and evaporated. The residue was passed through a short column of SiO₂ (about 20 g) using 30% ethyl acetate in hexane as eluant. The combined product fractions were evaporated Purification of the residue using HPLC using 20% ethyl acetate in hexane on Waters μ-porasil column afforded two isomers.

Less Polar Isomer: p.m.r. (CDCl₃): 0.7 (d, 3H), 1.0 (t, 3H), 1.6 (m, 2H), 1.8–2.2 (m, 4H), 2.6 (s, 3H), 2.7 (t, 2H), 3.1 (t, 2H), 3.3 (s, 3H), 3.5 (s, 3H), 4.1 (t, 2H), 4.7 (s, 1H), 5.6 (d, 1H), 6.3 (d, 1H), 7.0–7.4 (m, 9H), 7.6 (d, 1H), 12.8 (s, 1H).

More Polar Isomer: p.m.r. (CDCl₃): (d, 3H), 1.5 (m, 2H), 2.0–2.5 (m, 4H), 2.6 (s, 3H), 2.65 (t, 2H), 3.1 (t, 2H), 3.4 (s, 3H), 3.65 (s, 3H), 4.1 (t, 2H), 4.7 (s, 1H), 5.6 (d, 1H), 6.3 (d, 1H), 7.0 (m, 2H), 7.4 (s, 5H), 7.6 (d, 1H), 12.8 (s, 1H).

B. Preparation of the (+)-isomer of Sodium (beta S*, gamma R*)-4-(3-(4-acetyl-3-hydroxy-2-propylphenoxy)propylthio-gamma-hydroxy-beta-methylbenzenebutanoate A solution of least polar isomer from Step A (200 mg) in MeOH (5 ml), THF (5 ml) and 1N NaOH (1 ml) was stirred at room temperature. After 2 hours 1N NaOH (5 ml) was added. After 4 hours the reaction mixture was evaporated and redissolved in H₂O(2 ml). The solution was applied to an XAD column (30 ml resin). The column was washed with H₂O (200 ml) and the product was then eluted with MeOH (150 ml). Evaporation of the MeOH afforded the title compound as an oil.

$[\alpha]_D + 9.5°$ (c=2.0, MeOH).

C. Preparation of the (−)-isomer of Sodium (beta S*, gamma R*)-4-(3-(4-acetyl-3-hydroxy-2-propylphenoxy)propylthio-gamma-hydroxy-beta-methylbenzenebutanoate When the same procedure as described for the least polar isomer was applied to the more polar isomer from Step A (155 mg) there was obtained the title compound as an oil.

$[\alpha]_D − 9.2°$ (c=2.0, MeOH).

EXAMPLE 75

(Beta S*, gamma R*)-4-(3-(4-acetyl-3-hydroxy-2-propylphenoxy)propylthio)-gamma-hydroxy-beta-methylbenzenebutanoic acid gamma lactone A: Preparation of 4-methoxy-gamma-oxobenzenebutanoic Acid Anisole (70.0 g) and succinic anhydride (65.0 g) were dissolved in 1,2-dichloroethane (1 liter) and the mixture was cooled to 0° C. To the resulting suspension there was added, in portions, AlCl$_3$ (172 g) and the resulting mixture was stirred with a mechanical stirrer for 1 hour. The mixture was then poured into a mixture of ice and water (about 1 liter) containing 50 ml of concentrated HCl. The resulting white solid was collected by filtration, washed with water and air dried to yield the title compound, mp 145°-147° C.

B: Preparation of 4-hydroxy-gamma-oxobenzenebutanoic acid, methyl ester

A mixture of the compound from Step A (77.3 g), 48% HBr (310 ml), and acetic acid (620 ml) was heated under reflux for 18 hours. The resulting mixture was cooled to room temperature and poured into 3 liters of water. The resulting solution was extracted with ethyl acetate (3×500 ml). The 200 ml), dried over Na$_2$SO$_4$, the solvents were removed by evaporation and the residue was dissolved in 10% HCl/methanol (500 ml). After 1 hour at room temperature the volatile components were removed by evaporation in vacuo. The resulting residue was triturated with hexane to yield the title compound, mp 115°-116°.

C: Preparation of 4-dimethylthiocarbamoyloxy-gamma-oxobenzenebutanoic acid, methyl ester A solution of the product from Step B, 25 g, in anhydrous dimethylformamide (DMF) (300 ml) was cooled to 0° and 99% NaH, 3.46 g, was added in two portions. The mixture was stirred for 1 hour at 0° then dimethylthiocarbamoyl chloride, 19.3 g, was added and the mixture heated at 90° under a N$_2$ atmosphere for 1.5 hours. The mixture was cooled to room temperature and diluted with water to 1,200 mL. The resulting solution was then extracted with ethyl acetate (3×50 ml). The combined organic layers were washed with brine and then dried over Na$_2$SO$_4$ and evaporated to dryness in vacuo to yield a residue which was purified by chromatography on silica gel to yield the title compound, mp 62°-64°.

D: Preparation of 4-dimethylcarbamoylthio-gamma-oxobenzenebutanoic acid, methyl ester The compound from Step C, 29.6 g, was heated at 200° for 10 hours under an N$_2$ atmosphere. The mixture was cooled to room temperature, dissolved in methylene chloride and purified by chromatography on silica gel to provide the title compound, mp 98°-100°.

E: Preparation of methyl 4-dimethylcarbamoylthio-gamma-oxo-beta-methylbenzenebutanoate The compound from Step D, (10.0 g, 33.9 mmoles) was dissolved in THF (100 ml) and added dropwise to a stirred mixture of potassium hydride (1.6 g, 40.7 mmoles) in THF (10 ml) at −45° C. The reaction mixture was warmed to 0° to initiate the reaction, then cooled to −45° C. After 30 minutes, the reaction mixture was warmed to 0° C., and stirred for 10 minutes A solution of methyl iodide (3.17 ml, 50.9 mmoles) in THF (10 ml) was added slowly to the cold solution. The mixture was stirred at 0° for one hour. The reaction mixture was diluted with ether, washed with water, brine, dried and evaporated to yield an oil which was purified by HPLC to yield the title compound.

Analysis, calculated: C, 58.23; H, 6.19; N, 4.53; S, 10.36. Observed: C, 58.43; H, 6 31; N, 4.76; S, 10.39.

F: Preparation of (beta S*, gamma R*) 4-dimethylcarbamoylthio-gamma-hydroxy-beta-methylbenzenebutanoic acid gamma lactone (cis isomer) and (beta R*, gamma R*) 4-dimethylcarbamoylthio-gamma-hydroxy-beta-methylbenzenebutanoic acid gamma lactone (trans isomer)

To a solution of the compound from Step E above (10.4 g, 33.7 mmoles) in methanol (150 ml) was added cesium chloride monohydrate (50 mg). The solution was cooled to −20° and sodium borohydride (640 mg, 16.8 mmoles) was added in portions. The reaction mixture stirred at −20° for two hours. 2N NaOH (50 ml) was added and the mixture stirred at room temperature for one hour. The mixture was diluted with water (500 ml), cooled to 0°, acidified with concentrated HCl and extracted with ethyl acetate (3×). The combined organic extracts were washed with brine, dried and concentrated to an oil. The oil was dissolved in methylene chloride (150 ml) and trifluoroacetic acid (1 ml) was added. The reaction mixture stirred at room temperature for one hour. The reaction mixture was evaporated to an oil which crystallized on standing. The solid was purified by HPLC to afford pure cis (mp 116°-118°) and pure trans (m.p. 74°-76°) isomers of the title compound.

G: Preparation of (beta S*, gamma R*)-4-(3-(4-acetyl-3-hydroxy-2-propylphenoxy)propylthio)-gamma-hydroxy-beta-methylbenzenebutanoic acid The cis-isomer of the compound of Step F above (4.50 g, 16.1 mmoles) was suspended in methanol (160 ml). To the suspension was added 2N NaOH (80 ml, 160 mmoles) and the mixture was heated at reflux for five hours. The mixture was cooled to room temperature and 4-(3-bromopropoxy) 3-propyl-2-hydroxyacetophenone (7.61 g, 24.2 mmoles) was added. The mixture stirred at room temperature for three hours, and was then heated at reflux for two hours. The reaction mixture was cooled to room temperature, diluted with water (500 ml), acidified with concentrated HCl and extracted with ethyl acetate (2×). The organic extracts were washed with brine, dried and concentrated to an oil. The oil was dissolved in methylene chloride (100 ml) and trifluoroacetic acid (1 ml) was added. The mixture stirred at room temperature for one hour. The solution was evaporated to an oil which was purified by HPLC to yield the title compound as a white solid, m.p. 92°-94°.

Analysis, calculated: C, 67.84; H, 6.83; S, 7.25. Observed: C, 67.75; H, 6.84; S, 7.47.

EXAMPLE 76

(Beta S , gamma R*)
4-(3-(4-acetyl-3-hydroxy-2-propylphenoxy)propylsulfonyl)-gamma-hydroxy-beta-methyl-benzenebutanoic acid gamma lactone The compound of Example 75, Step G (550 mg, 1.24 mmoles) was dissolved in methylene chloride (5 ml) and a solution of m-chloroperbenzoic acid (606 mg, 2.99 mmoles) in methylene chloride (5 ml) was added. The mixture stirred at room temperature for ten minutes and calcium hydroxide (440 mg, 5.95 mmoles) was added. The mixture stirred at room temperature for thirty minutes. The mixture was filtered, the solid washed with methylene chloride and the filtrate evaporated to yield an oil. Silica gel chromatography of the oil afforded the title compound as a white foam.

NMR (ppm) (CDCl$_3$): 12.65 (1H, s), 8.0 (2H, d), 7.4–7.6 (3H, t), 6.35 (1H, d), 5.65 (1H, d), 4.1 (2H, t), 3.3 (2H, t), 2.7–3.1 (2H, m), 2.55 (3H, s), 2.1–2.7 (5H, m), 1.1–1.6 (2H, m), 0.9 (3H, t), 0.7 (3H, d).

EXAMPLE 77

(Beta S*, gamma R*) sodium 4-(3-(4-acetyl-3-hydroxy-2-propylphenoxy)propylsulfonyl)-gamma-hydroxy-beta-methylbenzenebutanoate The compound of Example 76 (543 mg, 1.15 mmoles) was dissolved in THF (17 ml) and 1N NaOH (1.7 ml, 1.72 mmoles) was added. The mixture stirred for twelve hours at room temperature and was then concentrated to dryness. The residue was purified on XAD-8 resin to afford the title compound as a beige foam.

Analysis, calculated: C, 58.35; H, 6.07; S, 6.23. Observed: C, 58.28; H, 6.08; S, 6.13.

EXAMPLE 78

(Beta S*, gamma R*)-sodium 4-(3-(4-acetyl-3-hydroxy-2-propylphenoxy)propylthio)-gamma-hydroxy-beta-methyl-benzenebutanoate Following the procedure of Example 77, but substituting an equivalent amount of the compound of Example 75, Step G, for the compound of Example 76, there was obtained the title compound as a beige foam.

Analysis, calculated: C, 62.22; H, 6.48; S, 6.64. Observed: C, 62.34; H, 6.23; S, 6.74.

The sodium salt (4.66 g) was dissolved in water (50 ml), cooled to 0° C. and acidified with 1N HCl. This mixture was extracted with ethyl acetate (100 ml), the organic layer washed with brine, dried over Na$_2$SO$_4$ and concentrated in vacuo without heating to a volume of about 40 ml. This solution was then made up to 50 ml volume by adding more ethyl acetate.

To 2 ml of the above solution of the free acid was added a solution of LiOH.H$_2$O (17 mg) in water (1 ml) and tetrahydrofuran (1 ml). The resulting mixture was evaporated to dryness and the residue dried under vacuum to yield the lithium salt as a foam.

Analysis: Calculated: C, 64.37; H, 6.70; S, 6.87; Li, 1.49. Observed: C, 64.35; H, 6.52; S, 6.50; Li, 1.55.

Following the above procedure but using 22 mg of KOH, there was obtained the potassium salt monohydrate as a foam.

Analysis: Calculated: C, 58.12; H, 6.44; S, 6.20. Observed: C, 57.98; H, 6.18; S, 6.02.

Addition of 48 mg of N,N'-dibenzylethylenediamine in 1 ml of ethyl acetate to a 2 ml aliquot of the free acid solution prepared above resulted in the crystallization of the N,N'-dibenzylethylenediamine salt after several hours, m.p. 117°–118°.

Analysis: Calculated: C, 68.25; H, 7.29; N, 2.41; S, 5.52. Observed: C, 68.14; H, 7.22; N, 2.54; S, 5.87.

Addition of 30 mg of ethylenediamine in 1 ml ethyl acetate to a 2 ml aliquot of the free acid solution and standing for 2 days at room temperature gave the crystalline ethylene diamine salt, m.p. 104°–106°.

Analysis Calculated: C, 63.65; H, 7.39; N, 2.85; S, 6.53. Observed: C, 64.14; H, 7.13; N, 2.50; S, 6.60.

The lactone from Example 75, Step G (442 mg) was stirred under nitrogen in a solution of tetrahydrofuran-methanol-2N NaOH (3 ml-1 ml-0.6 ml) for 3 hours at 25°. The reaction mixture was evaporated to dryness, the residue dissolved in 2.5 ml. H$_2$O and the pH adjusted to 8±0.1 by addition of 0.5N HCl. To the resulting solution was added CaCl$_2$ (55 mg) in water (2 ml) with vigorous stirring After 1 hour the resulting crystals of the calcium salt monohydrate were collected by filtration and dried; m.p. 148°–150°.

Analysis: Calculated: C, 61.45; H, 6.60; S, 6.56; Ca, 4.10. Observed: C, 61.92; H, 6.92; S, 6.41; Ca, 4.07.

Using similar techniques the magnesium, aluminum, N-methylglucamine, diethanolamine and choline salts were also prepared.

EXAMPLE 79

(Beta R*, gamma R*)
4-(3-(4-acetyl-3-hydroxy-2-propylphenoxy)propylthio)-gamma-hydroxy-beta-methylbenzenebutanoic acid gamma lactone Following the procedure of Example 75, Step G, but substituting the trans-lactone of Step F for the cis-lactone of Step F, there was obtained the title compound as an oil.

NMR (ppm) (CDCl$_3$): 12.75 (1H, s), 7.6 (1H, d), 7.2–7.5 (4H, dd), 6.4 (1H, d), 4.9 (1H, d), 4.15 (2H, t), 3.15 (2H, t), 2.6 (3H, s), 2.0–3.0 (7H, m), 1.3–1.8 (2H, m), 1.2 (2H, d), 0.95 (3H, t).

EXAMPLE 80

(Beta R*, gamma R*)
4-(3-(4-acetyl-3-hydroxy-2-propylphenoxy)propylsulfonyl)-gamma-hydroxy-beta-methylbenzenebutanoic acid gamma lactone Following the procedure of Example 76, but substituting an equivalent amount of the compound of Example 79, for the compound of Example 75, there was obtained the title compound as a white foam.

NMR (ppm) (CDCl$_3$): 12.75 (1H, s), 8.05 (2H, d), 7.6 (3H, d), 6.4 (1H, d), 5.05 (1H, d), 4.15 (2H, t), 3.4 (2H, t), 2.65 (3H, s), 2.1–2.9 (7H, m), 1.25–1.7 (2H, m), 1.25 (3H, d), 0.9 (3H, t).

EXAMPLE 81

Sodium (beta R*, gamma R*)
4-(3-(4-acetyl-3-hydroxy-2-propylphenoxy)propylsulfonyl)-gamma-hydroxy-beta-methylbenzenebutane Following the procedure of Example 77, but substituting an equivalent amount of the compound of Example 80 for the compound of Example 76, there was obtained the title compound as a beige foam.

Analysis, calculated: C, 58.28; H, 6.08; S, 6.13. Observed: C, 58.10; H, 6.07; S, 6.37.

EXAMPLE 82

Sodium (beta R, gamma R*)-4-(3-(4-acetyl-3-hydroxy-2-propylphenoxy)propylthio)-gamma-hydroxy-beta-methyl-benzenebutanoate Following the procedure of Example 78, but substituting an equivalent amount of the compound of Example 79 for the compound of Example 75, Step G, there was obtained the title compound as a beige foam.

Analysis, calculated: C, 62.34; H, 6.23; S, 6.74. Observed: C, 62.40; H, 6.30; S, 6.87.

EXAMPLE 83

(Alpha S*, beta R*, gamma R)-4-(3-(4-acetyl-3-hydroxy-2-propylphenoxy)propylthio)-gamma-hydroxy-alpha, beta-dimethyl-benzenebutanoic acid gamma lactone A: (Alpha S*, beta R*) 4-(3-bromopropylthio)-gamma-oxo-alpha,beta-dimethyl-benzenebutanoic acid 3-Bromopropylthiobenzene (4.62 g, 20.0 mmoles) and meso-2,3-dimethyl succinic anhydride (2.56 g, 20.0 mmoles) were dissolved in dichloroethane (100 ml) and cooled to 0°. Aluminum chloride (5.32 g, 40.0 mmoles) was added to the solution and the reaction mixture stirred at room temperature for twelve hours The mixture was poured into ice-water (300 ml) and acidified with 6N HCl (30 ml). Methylene chloride (200 ml) was added and the mixture stirred for two hours. The organic layer was collected The aqueous layer was extracted with methylene chloride and the combined organics were washed with brine, dried ((Na$_2$SO$_4$) and concentrated, to afford the title compound.

NMR (ppm) (CDCl$_3$): 1.23 (3H, d), 1.30 (3H, d), 2.23 (2H, m), 2.8-3.3 (3H, m), 3.4-3.8 (3H, m), 7.37 (2H, d), 7.93 (2H, d), 10.3 (1H, broad).

B: (Alpha S*, beta R*, gamma R*)-4-(3-bromopropylthio)-gamma-hydroxy-alpha, beta-dimethylbutanoic acid gamma lactone To a solution of the compound of Step A above (5.2 g, 14.7 mmoles) in dioxane (20 ml) and water (5 ml) at 0° was added 1N NaOH (15 ml). Sodium borohydride (0.6 g, 15.0 mmoles) was added and the mixture stirred at room temperature for one hour. Cesium chloride (20 mg) was added and the mixture stirred for ten hours The reaction mixture was acidified with concentrated HCl and extracted with ether. The organic extracts were concentrated, dissolved in methylene chloride (20 ml) and trifluoroacetic acid (2 drops) was added. The solution stirred at room temperature for thirty minutes, was washed with brine and dried (Na$_2$SO$_4$). The resulting lactones were separated by HPLC to yield (a) a less polar lactone the (alpha R*, beta R*, gamma R*) isomer of the title compound and (b) a more polar lactone NMR analysis confirmed the more polar lactone product (b) as the title compound.

NMR (ppm) (CDCl$_3$): 0.53 (3H, d), 1.23 (3H, d), 2.17 (2H, m), 2.67-3.17 (4H, m), 3.53 (2H, t), 5.50 (1H, d, J=5Hz), 7.23 (2H, d), 7.40 (2H, d).

C: Preparation of sodium (alpha S*, beta R*, gamma R*)-4-(3-bromopropylthio)-gamma-hydroxy,alpha, beta-dimethylbenzenebutanoate The more polar lactone of Step B above (822 mg, 2.40 mmoles) was dissolved in THF (20 ml) and treated with 2N NaOH (1.3 ml, 2.6 mmoles) at room temperature for fifteen hours The solvent was removed in vacuo. The residue was dissolved in methanol and again concentrated in vacuo to yield the title compound as a foam.

This compound was used without further purification or characterization in the next step.

D: (Alpha S*, beta R*, gamma R*)-4-(3-(4-acetyl-3-hydroxy-2-propylphenoxy)propylthio)-gamma-hydroxy-alpha, beta-dimethylbenzenebutanoic acid gamma lactone 2,4-Dihydroxy-3-propylacetophenone (450 mg, 2.32 mmoles) the compound of Step C above (890 mg, 2.32 mmoles) and potassium carbonate (1.09 g, 7.24 mmoles) were refluxed in methyl ethyl ketone (30 ml) for four hours. The mixture was cooled to room temperature and was poured into ice-water The mixture was acidified with 6N HCl and extracted with methylene chloride The combined extracts were washed with brine and concentrated in vacuo. The residue was dissolved in methylene chloride (20 ml) and trifluoroacetic acid (5 drops) was added. After five minutes the solution was washed with water, 0.1N NaOH and brine. The organic layer was dried (Na$_2$SO$_4$) and concentrated in vacuo. The residue was purified by chromatography on silica gel to afford the title compound.

NMR (ppm) (CDCl$_3$): 0.57 (3H, d), 0.93 (3H, t), 1.23 (3H, d), 1.37-1.67 (2H, m), 2.0-2.3 (2H, m), 2.57 (3H, s), 2.5-3.0 (4H, m), 3.13 (2H, t), 4.13 (2H, t), 5.45 (1H, d, J=5Hz), 6.37 (1H, d, J=9Hz), 7.17 (2H, d, J=8Hz), 7.33 (2H, d, J=8Hz), 7.53 (1H, d, J=9Hz), 12.70 (1H, s).

EXAMPLE 84

Sodium (alpha S*, beta R*, gamma R*)-4(3-(4-acetyl-3-hydroxy-2-propylphenoxy)propylthio)-gamma-hydroxy-alpha, beta-dimethylbenzenebutanoate The lactone of Example 83, Step D (487 mg, 1.067 mmoles) was dissolved in THF (10 ml) and methanol (2 ml). To this solution was added 1N NaOH (2 ml) and the reaction mixture stirred at room temperature for twenty one hours. The mixture was concentrated in vacuo and the residue purified by chromatography on XAD-8 resin to yield the title compound.

Analysis, calculated: C, 62.88; H, 6.70; S, 6.46. Observed: C, 63.02; H, 6.86; S, 6.37.

EXAMPLE 85

D,L-4-(3-(4-acetyl-3-hydroxy-2-propylphenoxy)-propylthio)-gamma-hydroxybenzenebutanoic acid gamma lactone A: Preparation of 4-mercapto-gamma-oxobenzenebutanoic acid, methyl ester Sodium (280 mg, 12.18 mmoles) was dissolved in anhydrous methanol (50 ml). To the resulting solution was added the compound of Example 75, Step D (5.0 g). The mixture was stirred at room temperature for twelve hours and poured into a mixture of water (30 ml) and concentrated HCl (7 ml). The resulting yellow solid was collected by filtration, washed with water and dried to afford the title compound, m.p. 83°-84°.

B: Preparation of 4-((3-(4-Acetyl-3-hydroxy-2-propylphenoxy)propylthio)-gamma-oxobenzenebutanoic acid 2-Hydroxy-3-propyl-4 (3-bromopropyloxy)acetophenone (0.76 g, 2.4 mmoles) and the compound of Step A above (0.6 g, 2.4 mmoles) were dissolved in THF (50 ml) and heated at reflux for forty-eight hours in the Presence of 1.0 equivalent of Potassium carbonate. The reaction mixture was filtered and concentrated in vacuo. The residue was purified by chromatography on silica gel and saponified with potassium hydroxide (1.5 equivalents) in a mixture of methanol and water (25 ml, 10:1). The reaction mixture was concentrated in vacuo, the residue dissolved in water and acidified with citric acid. The aqueous phase was extracted with ethyl acetate. The organic phase was washed with brine, dried (Na$_2$SO$_4$) and evaporated to dryness. The residue was triturated with hexane and the solid collected by filtration to afford the title compound.

Analysis, calculated: C, 64.98; H, 6.14; S, 7.23. Observed: C, 65.09; H, 6.09; S, 7.28.

C: Preparation of D,L-4-(3-(4-acetyl-3-hydroxy-2-propylphenoxy)propylthio)-gamma-hydroxy-benzenebutanoic acid gamma lactone The compound of Step B above (4.0 g, 8.99 mmoles) was dissolved in a mixture of THF and ethanol (110 ml, 10:1). To this solution was added sodium borohydride (440 mg, 11.63 mmoles) The reaction mixture stirred for twenty-four hours and was concentrated in vacuo. The residue was treated with chloroform (40 ml) and acidified with trifluoroacetic acid. After two hours the reaction mixture was concentrated in vacuo and the residue purified by HPLC to afford the title compound.

Analysis, calculated: C, 67.27; H, 6.59; S, 7.41. Observed: C, 67.49; H, 6.90; S, 7.81.

EXAMPLE 86

D,L-4-(3-(4-acetyl-3-hydroxy-2-propylphenoxy)-propylsulfonyl)-gamma-hydroxybenzenebutanoic acid gamma lactone A: Preparation of 4-(3-(4-acetyl-3-hydroxy-2-propylphenoxy)propylsulfonyl)-gamma-oxo-benzenebutanoic acid The ester prepared in Example 85 Step B (1.83 g, 4 mmoles), was dissolved in methylene chloride (50 ml) and treated at room temperature with m-chloroperbenzoic acid (1.73 g, 2.5 equivalents) for two hours The reaction mixture was concentrated in vacuo and purified by chromatography on silica gel to yield the methyl ester of the title compound, which, upon saponification with NaOH in methanol, yielded the title compound.

Analysis, calculated: C, 60.48; H, 5.92; S, 6.72 Observed: C, 60.51; H, 5.90; S, 6.48

B: Preparation of D,L-4-(3-(4-acetyl-3-hydroxy-2-propylphenoxy)propylsulfonyl)-gamma-hydroxybenzenebutanoic acid gamma lactone The compound of Step A above (5.0 g, 10.5 mmoles) was dissolved in a mixture of THF-ethanol (105 ml, 20:1). To this solution was added sodium borohydride (440 mg, 11.63 mmoles) and the reaction mixture stirred at room temperature for 16 hours. The mixture was concentrated in vacuo and dissolved in chloroform (100 ml) containing trifluoroacetic acid (2 ml). This solution stirred at room temperature for two hours and was concentrated in vacuo. The residue was purified by HPLC to afford the title compound, m.p 131°–133°. Analysis, calculated: C, 62.59; H, 6.13; S, 6.96. Observed: C, 62 62; H, 6.09; S, 6.74.

Using the above described methodology and starting with the appropriately substituted 2,4-dihydroxyacetophenone, the following compounds are also prepared:

EXAMPLE 87

4-((3-(4-acetyl-6-fluoro-3-hydroxy-2-propylphenoxy) propyl)thio)-gamma-oxobenzenebutanoic acid.

EXAMPLE 88

4-((3-(4-acetyl-6-chloro-3-hydroxy-2-propylphenoxy) propyl)thio)-gamma-oxobenzenebutanoic acid.

EXAMPLE 89

4-(3-(4-acetyl-6-chloro-3-hydroxy-2-propylphenoxy) propyl)thio)-gamma-oxobenzenebutanoic acid.

EXAMPLE 90

4-((3-(4-acetyl-6-bromo-3-hydroxy-2-propylphenoxy) propyl)thio)-gamma-oxobenzenebutanoic acid.

EXAMPLE 91

4-(3-(4-acetyl-6-bromo-3-hydroxy-propylphenoxy) propylsulfonyl)-gamma-oxobenzenebutanoic acid.

EXAMPLE 92

4-((3-(4-acetyl-3-hydroxy-6-methyl-2-propylphenoxy) propyl)thio)-gamma-oxobenzenebutanoic acid.

EXAMPLE 93

(Beta S*, gamma R*)
4-(3-(4-acetyl-6-fluoro-3-hydroxy-2-propylphenoxy)-propylthio-gamma-hydroxy-beta-methylbenzenebutanoic acid Sodium salt: Analysis: Calculated: C, 59.99; H, 6.04; F, 3.80; S, 6.41. Found: C, 59.25; H, 6.03; F, 3.72; S, 6.53.

EXAMPLE 94

(Beta S*, gamma R*) 4-(3-(4-acetyl-5-chloro-3-hydroxy-2-propylphenoxy)propylthio)-gamma-hydroxy-beta-methylbenzenebutanoic acid.

EXAMPLE 95

(Beta S*, gamma R*) 4-(3-(4-acetyl-3-hydroxy-6-methyl-2-propylphenoxy)propylthio)-gamma-hydroxy-beta-methylbenzenebutanoic acid.

EXAMPLE 96

(Beta S*, gamma R*) 4-(3-(4-acetyl-6-ethyl-3-hydroxy-2-propylphenoxy)propylthio)-gamma-hydroxy-beta-methylbenzenebutanoic acid.

EXAMPLE 97

4-(3-(4-acetyl-6-fluoro-3-hydroxy-2-propylphenoxy) propyloxy)-gamma-hydroxy-beta,beta-dimethylbenzene-butanoic acid.

EXAMPLE 98

4-(3-(4-acetyl-6-chloro-3-hydroxy-2-propylphenoxy) propyloxy)-gamma-hydroxy-beta,beta-dimethylbenzene-butanoic acid.

EXAMPLE 99

4-(3-(4-acetyl-3-hydroxy-6-methyl-2-propylphenoxy) propyloxy)-gamma-hydroxy-beta,beta,dimethylbenzene-butanoic acid.

EXAMPLE 100

4-(3-(4-acetyl-6-fluoro-3-hydroxy-2-propylphenoxy) propylthio)-gamma-hydroxy-beta,beta-dimethylbenzene-butanoic acid.

EXAMPLE 101

4-(3-(4-acetyl-5-chloro-3-hydroxy-2-propylphenoxy)propylthio)-gamma-hydroxy-beta,beta-dimethylbenzene-butanoic acid.

EXAMPLE 102

4-(3-(4-acetyl-3-hydroxy-6-methyl-2-propylphenoxy)propylthio)-gamma-hydroxy-beta,beta-dimethylbenzenebutanoic acid.

EXAMPLE 103

Sodium (beta S*, gamma R*) 4-(3-(4-acetyl-3-hydroxy-2-propylphenoxy)propyloxy)-gamma-hydroxy-beta-methylbenzenebutanoate A: Preparation of methyl 4-hydroxy-gamma-oxo-beta-methylbenzenebutanoate A mixture of the ester from Example 70, Step A (8.15 g), 48% HBr (40 ml) and acetic acid (80 ml) was refluxed for 4 days, then poured into water (250 ml) and extracted with ethyl acetate. The extracts were washed with water and dried ($Na_2SO_4$) and evaporated to an oil which was treated with 10% HCl in methanol (150 ml) for 18 hours. The volatiles were removed by evaporation and the residue was taken up in $CH_2Cl_2$, washed with water, brine, dried, evaporated to dryness then purified by chromatography on silica gel to provide the title compound, mp 89°–91° C.

B: Preparation of methyl 4(3-bromopropoxy)-gamma-oxo-beta-methylbenzenebutanoate The mixture of the phenol from Step A (4.0 g) 1,3-dibromopropane (18.2 ml), potassium carbonate (7.5 g) and methyl ethyl ketone (100 ml) was refluxed for 1 hour. The mixture was filtered, concentrated in vacuo and the residue was purified by chromatography on silica gel to provide the title compound as an oil.

C: Preparation of (beta S*, gamma S*) and (beta S*, gamma R*) 4-(3-bromopropyloxy)-gamma-hydroxy-beta-methylbenzenebutanoic acid gamma lactones The ketone from Step B (5.0 g) in methanol (70 ml) was treated with ceric chloride monohydrate (50 mg) and the mixture was cooled to −20° C. followed by addition of sodium borohydride (277 mg). After stirring 2 hours at −20° C. the mixture was warmed to ambient temperature, diluted with water (150 ml) and 1N HCl (10 ml), then extracted with $CH_2Cl_2$. The extracts were washed with brine and evaporated to an oil which was treated in methanol (50 ml) and 2N NaOH (22 ml) for 1 hour. The mixture was diluted with water (750 ml), acidified, and extracted with EtOAc. The organic extracts were washed with brine, dried ($Na_2SO_4$) evaporated to an oil which was dissolved in dichloromethane (100 ml) and trifluoroacetic acid (1 ml). After 30 minutes the mixture was evaporated to dryness and the residue was purified by chromatography on silica gel to provide the (beta S*, gamma S*)-isomer of the title compound (less polar).

NMR ($CDCl_3$): 1.15 (3H, d), 2.1–2.9 (5H, m), 3.55 (2H, t), 4.1 (2H, t), 4.85 (1H, d), 6.9 (2H, d), 7.25 (2H, d), and the (beta S*, gamma R*) isomer of the title compound (more polar), NMR ($CDCl_3$): 0.7 (3H, d), 2.2–2.9 (5H, m), 3.6 (2H, t), 4.1 (2H, S), 5.5 (1H, d), 6.9 (2H, d), 7.1 (2H, d).

D: Preparation of (Beta S*, gamma R*) 4-(3-(4-acetyl-3-hydroxy-2-propylphenoxy)propyloxy)-gamma-hydroxy-beta-methylbenzenebutanoic acid gamma lactone The more polar isomer from Step C (1.2 g) and 2,4-dihydroxy-3-propylacetophenone (1.19 g) was refluxed in methyl ethyl ketone (20 ml) and potassium carbonate (2 g) for 12 hours. The mixture was filtered, concentrated and purified by chromatography on silica gel to provide the title compound as an oil; NMR ($CDCl_3$): 0.7 (3H, d), 0.9 (3H, t), 1.5 (2H, m), 2.1–2.9 (7H, m), 2.5 (3H, s), 4.05–4.3 (4H, m), 5.5 (1H, d), 6.4 (1H, d), 6.85 (2H, d), 7.1 (2H, d), 7.55 (1H, d), 12.65 (1H, s).

E: Preparation of Sodium (Beta S*, gamma R*) 4-(3-(4-acetyl-3-hydroxy-2-propylphenoxy)propyloxy)-gamma-hydroxy-beta-methylbenzenebutanoate The lactone from Step D (1.19 g) was saponified in 1N NaOH (4 ml), THF (15 ml) and methanol (2 ml) for 12 hours The mixture was concentrated in vacuo and the residue in water was purified on XAD-8 resin to provide the title compound as a foam.

Analysis, calculated: C, 64.36; H, 6.70. Observed: C, 64.26; H, 6.93.

Using the lactone from Step D and following the procedure of Example 78 the ethylenediamine salt was also prepared:

Analysis: Calculated: C, 65.80; H, 7.65; N, 2.95. Observed: C, 65.58; H, 7.50; N, 3.09.

Using the above described methodologies, the following compounds are also prepared:

EXAMPLE 104

4-(3-(4-acetyl-3-hydroxy-2-propylphenoxy)propylthio)-3-propyl-gamma-oxo-benzenebutanoic acid, m.p. 148°–149°.

Analysis, calculated: C, 66.64; H, 7.04; S, 6.59. Observed: C, 66.89; H, 7.22; S, 6.25.

EXAMPLE 105

4-(3-(4-acetyl-3-hydroxy-2-propylphenoxy)propylsulfonyl-3-propyl-gamma-oxo-benzenebutanoic acid, m.p. 156°–158° C.

Analysis, calculated: C, 62.53; H, 6.61; S, 6.18. Observed: C, 62.35; H, 6.62; S, 5.99.

EXAMPLE 106

(Beta R*, gamma S*) sodium 4(3(4-acetyl-3-hydroxy-2-propylphenoxy)propylthio)-3-fluoro-gamma-hydroxy-beta-methylbenzenebutanoate.

EXAMPLE 107

(Beta R*, gamma S*) sodium 4-(3-(4-acetyl-3-hydroxy-2-propylphenoxy)propylthio)-3-bromo-gamma-hydroxy-beta-methylbenzenebutanoate.

(Beta R*, gamma S*) sodium 4-(3-(4-acetyl-3-hydroxy-2-propylphenoxy)propylthio)-3-chloro-gamma-hydroxy-beta-methylbenzenebutanoate.

EXAMPLE 109

4-(3-(4-acetyl-3-hydroxy-2-propylphenoxy)propylsulfonyl)-gamma-oxo-beta,beta-dimethylbenzenebutanoic acid.

EXAMPLE 110

D,L-Sodium 4-(3-(4-acetyl-3-hydroxy-2-propylphenoxy)propylsulfonyl)-gamma-hydroxy-beta,beta-dimethyl benzenebutanoate.

EXAMPLE 111

4-(3-(4-acetyl-3-hydroxy-2-propylphenoxy)propylthio)-3-propyl-gamma-oxo-beta,beta-dimethylbenzenebutanoic acid.

EXAMPLE 112

D,L Sodium 4-(3-(4-acetyl-3-hydroxy-2-propylphenoxy) propylthio)-3-propyl-gamma-hydroxy-beta,-beta-dimethylbenzenebutanoate.

EXAMPLE 113

Sodium 4-(3-(4-acetyl-3-hydroxy-2-propylphenoxy) propylthio)-3-fluoro-gamma-oxo-beta,beta-dimethyl benzenebutanoate.

EXAMPLE 114

D,L Sodium 4(3-(4-acetyl-3-hydroxy-2-propylphenoxy) propylthio)-3-fluoro-gamma-hydroxy-beta,-beta-dimethylbenzenebutanoate.

EXAMPLE 115

4-(3-(4-acetyl-3-hydroxy-2-propylphenoxy)propylthio)-3-chloro-gamma-oxo-beta,beta-dimethylbenzenebutanoic acid.

EXAMPLE 116

D,L.-Sodium 4-(3-(4-acetyl-3-hydroxy-2-propylphenoxy) Propylthio)-3-chloro-gamma-hydroxy-beta,-beta-dimethylbenzenebutanoate.

EXAMPLE 117

D,L-Sodium 4-(3-(4-acetyl-3-hydroxy-2-propylphenoxy)propylthio)-3-bromo-gamma-hydroxy-beta,-beta-dimethylbenzenebutanoate.

EXAMPLE 118

D,L-Sodium-4-(3-(4-acetyl-3-hydroxy-2-propylphenoxy)propyloxy)-3-fluoro-gamma-hydroxy-beta,-beta-dimethylbenzenebutanoate.

EXAMPLE 119

D,L-Sodium 4-(3-(4-acetyl-3-hydroxy-2-propylphenoxy) propyloxy)-3-bromo-gamma-hydroxy-beta,-beta-dimethylbenzenebutanoate.

EXAMPLE 120

D,L-Sodium 4-(3-(4-acetyl-3-hydroxy-2-propylphenoxy) propyloxy)-3-chloro-gamma-hydroxy-beta,-beta-dimethylbenzenebutanoate.

EXAMPLE 121

4-(3-(4-acetyl-3hydroxy-2-propylphenoxy)-propyloxy-3-fluoro-gamma-oxo-beta,beta-dimethylbenzenebutanoic acid.

EXAMPLE 122

4-(3-(4-acetyl-3-hydroxy-2-propylphenoxy)propyloxy)-3-chloro-gamma-oxo-beta,beta-dimethylbenzenebutanoic acid.

EXAMPLE 123

4-(3-(4-acetyl-3-hydroxy-2-propylphenoxy)propyloxy)-3-bromo-gamma-oxo-beta,beta-dimethylbenzenebutanoic acid.

EXAMPLE 124

4-(3-(4-acetyl-3-hydroxy-2-propylphenoxy)propyloxy)-3-propyl-gamma-oxo-beta,beta-dimethylbenzenebutanoic acid.

EXAMPLE 125

Sodium-(Beta R*, gamma S*) 3-(3-(4-acetyl-3-hydroxy-2-propylphenoxy)propylthio)-gamma-hydroxy-beta-methyl-benzenebutanoate.

EXAMPLE 126

D,L-sodium 3-(3-(4-acetyl-3-hydroxy-2-propylphenoxy) propylthio)-gamma-hydroxy-beta,beta-dimethyl-benzenebutanoate.

EXAMPLE 127

D,L-sodium 3-(3-(4-acetyl-3-hydroxy-2-propylphenoxy) propyloxy)-gamma-hydroxy-beta,beta-dimethylbenzenebutanoate.

EXAMPLE 128

3-(3-(4-acetyl-3-hydroxy-2-propylphenoxy)propylthio)-gamma-oxobenzenebutanoic acid

EXAMPLE 129

3-(3-(4-acetyl-3-hydroxy-2-propylphenoxy)propylthio)-gamma-oxo-beta,beta,dimethylbenzenebutanoic acid.

EXAMPLE 130

3-(3-(4-acetyl-3-hydroxy-2-propylphenoxy)propyloxy)-gamma-oxo-beta,beta-dimethylbenzenebutanoic acid.

EXAMPLE 131

(Beta R*, gamma S*) sodium 4-(3-(4-acetyl-3-hydroxy-2-propylphenoxy)propylthio)-gamma-hydroxy-beta-methylbenzene butanoate-S-oxide.

EXAMPLE 132

(Beta R*, gamma S*) 4-(3-(4-acetyl-3-hydroxy-2-propylphenoxy)propylthio)-3-propyl-gamma-hydroxy-beta-methylbenzenebutanoic acid.

EXAMPLE 133

4-(3-(4-acetyl-3-hydroxy-2-propylphenoxy)propylsulfonyl)-gamma-oxo-beta,beta-dimethylbenzenebutanoic acid.

EXAMPLE 134

D,L-4-(3-(4-acetyl-3-hydroxy-2-propylphenoxy)-propylsulfonyl)-gamma-hydroxy-beta,beta-dimethylbenzenebutanoic acid.

EXAMPLE 135

D,L-4-(3-(4-acetyl3-hydroxy-2-propylphenoxy)-propylthio)-3-propyl-gamma-oxo-beta,beta-dimethylbenzenebutanoic acid, methyl ester.

EXAMPLE 136

4-(3-(4-acetyl-3-hydroxy-2-propylphenoxy)propylthio)-3-fluoro-gamma-oxo-beta,beta-dimethyl-benzenebutanoic acid.

EXAMPLE 137

D,L-4-[4-(3-(4-acetyl-3-hydroxy-2-propylphenoxy) propylthio)-3-fluoro-gamma-hydroxy-beta,beta-dimethylbenzenebutanoic acid.

EXAMPLE 138

(3R*, 4S*) 4-[4-[3-(4-acetyl-3-hydroxy-2-propylphenoxy)propylthio]-3-fluorophenyl]-3-methyl-gamma-butyrolactone.

EXAMPLE 139

(3R*, 4S*) 4-[4-[3-(4-acetyl-3-hydroxy-2-propylphenoxy)propylthio]-3-chlorophenyl]-3-methyl-gamma-butyrolactone.

EXAMPLE 140

(3 R*, 4 S*) 4-[4-[3-(4-acetyl-3-hydroxy-2-propylphenoxy)propylthio]-3-bromophenyl]-3-methyl-gamma-butyrolactone.

EXAMPLE 141

(3 R*, 4 R*) 4-[4-[3-(4-acetyl-3-hydroxy-2-propylphenoxy)propylthio]-3-fluorophenyl]-3-methyl-gamma-butyrolactone.

EXAMPLE 142

(3 R*, 4 R*) 4-[4-[3-(4-acetyl-3-hydroxy-2-propylphenoxy)propylthio]-3-bromophenyl]-3-methyl-gamma-butyrolactone.

EXAMPLE 143

(3 R*, 4 R*) 4-[4-[3 (4-acetyl-3-hydroxy-2-propylphenoxy)propylthio]-3-chlorophenyl]-3-methyl-gamma-butyrolactone.

EXAMPLE 144

(3 R*, 4 S*) 4-[4-[3-(4-acetyl-3-hydroxy-2-propylphenoxy)propyloxy]-phenyl]-3-methyl-butyrolactone.

EXAMPLE 145

(Beta R*, gamma S*) 4-(3-(4-acetyl-3-hydroxy-2-propylphenoxy)propyloxy)-3-propyl-gamma-hydroxy-beta-methylbenzenebutanoic acid.

EXAMPLE 146

4-(3-(4-acetyl-3-hydroxy-2-propylphenylthio) propyloxy)-3-fluoro-gamma-oxo-butanoic acid.
m.p. 133°-134°.

EXAMPLE 147

4-(3-(4-acetyl-3-hydroxy-2-propylphenylthio) propyloxy)-3-fluoro-gamma-oxo-benzenebutanoic acid S-oxide. M.P. 156°-157°.

EXAMPLE 148

4-(3-(4-acetyl-3-hydroxy-2-propylphenylsulfonyl) propyloxy)-3-fluoro-gamma-oxo-benzenebutanoic acid. m.p. 182°-184°.

EXAMPLE 149

4-(3-(4-acetyl-3-hydroxy-2-propylphenylthio) propylthio)-gamma-oxo-benzenebutanoic acid.
m.p. 87°-88.5°.

EXAMPLE 150

4-(3-(4-acetyl-3-hydroxy-2-propylphenylthio) propylsulfonyl)-gamma-oxo-benzenebutanoic acid.
m.p. 135°-138°.

EXAMPLE 151

Resolution of Sodium (beta S*, gamma R*) 4-(3-(4-acetyl-3-hydroxy-2-propylphenoxy)propyloxy)-gamma-hydroxy-beta-methylbenzenebutanoate into the (+) isomer and the (−) isomer Follow the procedure of Example 74, but substitute the lactone of Example 103, Step D, for the lactone from Example 75, to obtain the (+) and (−) isomers of the title compound.

EXAMPLE 152

4-(3-(4-acetyl-3-hydroxy-2-propylphenoxy)propylthio)-gamma-oxo-beta-methylbenzenebutanoic acid, sodium salt Analysis: Calculated: C 62.48, H 6.08, S 6.67. Found: C 62.22, H 6.05, S 6.79.

EXAMPLE 153

4-(3-(4-acetyl-3-hydroxy-2-propylphenoxy)propylthio)delta-hydroxy-gamma-methylbenzenebutanol

EXAMPLE 154

4-(3-(4-acetyl-3-hydroxy-2-propylphenoxy)propylthio)gamma-oxo-beta-methylbenzenebutanoic acid-S-oxide, sodium salt dihydrate Analysis Calculated: C 56.38, H 6.25, S 6.02. Found: C 56.12, H 6.06, S 6.09.

EXAMPLE 155

4-(3-(4-acetyl-3-hydroxy-2-propylphenoxy)propylsulfonyl)-gamma-oxo-beta-methylbenzenebutanoic acid, sodium salt trihydrate Analysis: Calculated: C 53.03, H 6.13, S 6.00. Found: C 52.99, H 6.23, S 5.66.

EXAMPLE 156

4-(3-(4-acetyl-3-hydroxy-2-propylphenoxy)propylsulfonyl)-delta-hydroxy-gamma-methylbenzenebutanol.

EXAMPLE 157

4-(3-{4-acetyl-3-hydroxy-2-propylphenoxy)propylthio)-gamma-hydroxybenzenebutanoic acid m.p. 142°-143° C.
Analysis: Calculated: C 64.57, H 6.72, S 7.17. Found: C 64.61, H 6.71, S 7.18.

EXAMPLE 158

4-(3-(4-acetyl-3-hydroxy-2-propylphenoxy)propylthio)-delta-hydroxybenzenebutanol Analysis: Calculated: C 66.64, H 7.46, S 7.41. Found: C 66.65, H 7.40, S 7.30.

EXAMPLE 159

4-(3-(4-acetyl-3-hydroxy-2-propylphenoxy)propylsulfonyl)-gamma-hydroxybenzenebutanoic acid sodium salt hemihydrate m.p. 80°-90° C. (dec.)
Analysis: Calculated: C 56.46, H 5.92. Found: C 56.09, H 6.03.

EXAMPLE 160

4-(3-(4-acetyl-3-hydroxy-2-propylphenoxy)propylsulfonyl)-delta-hydroxybenzenebutanol Analysis: Calculated: C 62.05, H 6.94, S 6.90. Found: C 62.07, H 6.92, S 6.72.

EXAMPLE 161

(Beta R*, gamma S*)
4-(3-(4-acetyl-6-chloro-3-hydroxy-2-propylphenoxy)-propylthio)-gamma-hydroxy-beta-methylbenzenebutanoic acid sodium salt. 1.5 $H_2O$ Analysis: Calculated: C 55.19, H 6.11, Cl 6.52, S 5.89. Found: C 55.35, H 5.81, Cl 6.82, S 6.23.

EXAMPLE 162

($\beta$R, $\beta$S)
4-(3-(4-acetyl-3-hydroxy-2-propylphenoxy)propylthio)-$\gamma$-oxo-$\beta$-methyl-2-carboxybenzenebutanoic acid, disodium salt A: Preparation of 2-bromo-4-methylthiopropiophenone To a cooled (−5° C.) solution of 3-bromothioanisole (8.39 g) and propionyl chloride (8.78 g) in carbon disulfide (250 c.c.) was added portionwise over one hour aluminum chloride (27 g) and the suspension was stirred for 45 min at R.T. (room temperature). The carbon disulfide was decanted and replaced by dichloromethane (250 c.c.) and the solution cooled to 0° C.; ice was added followed by water and the organic layer separated and dried with $Na_2SO_4$. Removed of the solvent yielded a residue containing mainly the title compound and some of the isomeric 4-bromo-2-methylthiopropiophenone which could be eliminated by chromatography on silica. Yield of the title compound. N.M.R. $^1$H-250 MHz/$C_6D_6$

| N.M.R. $^1$H-250 MHz/$C_6D_6$ | | | |
|---|---|---|---|
| δ (p.p.m.) | # of H | m | J (Hz) |
| 7.2 | 1 | d | 1.8 |
| 6.71 | 1 | d.d. | 8.1 and 1.8 |
| 6.9 | 1 | d | 8.1 |
| 2.52 | 2 | q | 7.2 |
| 1.68 | 3 | s | |
| 1.07 | 3 | t | 7.2 |

B. Preparation of ($\beta$R, $\beta$S) methyl 2-bromo-4-methylthio-$\gamma$-oxo-$\beta$-methylbenzenebutanoate To a cooled (−78° C.) solution of 0.654M potassium hexamethyldisilazane in toluene (165 c.c.) and THF (150 c.c.) was added dropwise the ketone obtained from step A over a period of 45 min. After a further 20 min at −78° C. a solution of methyl bromoacetate (18 g) in THF (25 c.c.) was added dropwise and reacted for one hour at −78° C. The reaction mixture was then poured into ice-cold 1N HCl (1000 c.c.); extraction of the organics with ethyl acetate (3×200 c.c.) was followed by drying with brine and $Na_2SO_4$. Removal of the solvents in vacuo yielded a residue which was purified on silica gel to yield the title compound as an oil.

| N.M.R. $^1$H-250 MHz/$CDCl_3$ | | | |
|---|---|---|---|
| δ (p.p.m.) | # of H | m | J (Hz) |
| 7.17-7.52 | 3 | m | — |
| 3.67-3.8 | 4 | m | — |
| 2.8-3.0 | 1 | m | — |
| 2.4-2.5 | 4 | m | — |
| 1.1-1.2 | 3 | d | 5 |

C. Preparation of ($\beta$R, $\beta$S) methyl 2-bromo-4-mercapto-$\gamma$-oxo-$\beta$-methylbenzenebutanoate To a cooled (0° C.) solution of the sulfide obtained in step B (3.59 g) in chloroform (30 c.c.) was added m-chloroperoxybenzoic acid (1.87 g) and the suspension was stirred for 1 hr. It was than warmed up to R.T. and $Ca(OH)_2$ (1.11 g) was added and stirred for 45 min. Insolubles were filtered off and trifluoroacetic anhydride (10 g) was added to the filtrate and the mixture heated to reflux for 1 hr. Volatiles were removed in vacuo to yield a residue to which was added a solution of MeOH (50 c.c.) and triethylamine (50 c.c.); the mixture was then concentrated in vacuo to dryness and this process was repeated 3 times. The residue was finally taken up in ethyl acetate (100 c.c.) and washed with 1N HCl (3×25 c.c.), brine, dried and evaporated to dryness to yield the title compound as an oil which was used immediately in the following step.

D. Preparation of ($\beta$R, $\beta$S) methyl 4-(3-(4-acetyl-3-hydroxy-2-propylphenoxy)propylthio)-$\gamma$-oxo-$\beta$-methyl-2-bromobenzenebutanoate To a solution of the thiol from step C (2.9 g) and 3-(4-acetyl-3-hydroxy-2-propylphenoxy)propylbromide (3.74 g) in methyl ethyl ketone (25 c.c.) was added potassium carbonate (3.78 g, milled) and the suspension was refluxed for 2¼ hours, then stirred at R.T. for 12 hours. The mixture was diluted with ethyl acetate (25 c.c.) and the insolubles filtered off. The filtrate was concentrated to dryness in vacuo and the residue purified on silica gel to yield the title compound as an oil.

| N.M.R. $^1$H-250 MHz/$CDCl_3$ | | | |
|---|---|---|---|
| δ (p.p.m.) | # of H | m | J (Hz) |
| 12.73 | 1 | s | — |
| 7.59-7.63 | 1 | d | 8.3 |
| 7.25-7.55 | 3 | m | — |
| 6.4-6.47 | 1 | d | 8.3 |
| 4.1-4.2 | 2 | t | 5.5 |
| 3.65-3.7 | 4 | m | — |
| 3.18-3.24 | 2 | t | 5.5 |
| 2.1-3.0 | 9 | m | — |
| 1.5-1.65 | 2 | m | — |
| 1.15-2.12 | 3 | a | 6.5 |
| 0.9-1.0 | 3 | t | 5.5 |

Preparation of ($\beta$R, $\beta$S) methyl 4-(3-(4-acetyl-3-hydroxy-2-propylphenoxy)propylthio)-$\gamma$-oxo-$\beta$-methyl-2-cyanobenzenebutanoate A suspension of the bromide from step D (1.65 g) and copper cyanide (1.34 g) in N,N-dimethylformamide (DMF) (30 c.c.) was heated to 90° C. for 18 hours. DMF was removed in vacuo and the residue was purified on silica gel to yield the title compound as an oil.

| N.M.R. $^1$H-250 MHz/$CDCl_3$ | | | |
|---|---|---|---|
| δ (p.p.m.) | # of H | m | J (Hz) |
| 12.74 | 1 | s | — |
| 7.85-7.95 | 1 | d | 8.3 |
| 7.5-7.65 | 3 | m | — |
| 6.4-6.45 | 1 | d | 8.3 |
| 4.15-4.25 | 2 | t | 5.0 |
| 3.75-3.9 | 1 | m | — |
| 3.65 | 3 | s | — |
| 3.20-3.30 | 2 | t | 5.0 |
| 2.1-3.1 | 9 | m | — |
| 1.47-1.65 | 2 | m | — |
| 1.2-1.28 | 3 | d | 6.5 |
| 0.9-1.0 | 3 | t | 5.5 |

F. Preparation of ($\beta$R, $\beta$S) 4-(3-(4-acetyl-3-hydroxy-2-propylphenoxy)propylthio)-$\gamma$-oxo-$\beta$-methyl-2-carboxybenzenebutanoic acid, disodium salt A suspension of the ester from step E (133 mg) in THF (3 c.c.), MeOH (1 c.c.), H₂O (1 c.c.) and 2N NaOH (670 μL) was refluxed for 18 hours. It was then cooled to R.T. and concentrated to dryness in vacuo. The residue was absorbed on XAD-8 neutral resin in water, washed with water and eluted off with ethanol. Removal of the solvent from the ethanolic fraction yielded the title compound as a foam.

| N.M.R. ¹H-250 MHz/D₂O | | | |
|---|---|---|---|
| δ (p.p.m.) | # of H | m | J (Hz) |
| 7.55–7.65 | 1 | d | 8.3 |
| 7.25–7.5 | 3 | m | — |
| 6.35–6.45 | 1 | d | 8.3 |
| 4.0–4.1 | 2 | t | — |
| 3.4–3.5 | 1 | m | — |
| 3.1–3.2 | 2 | t | — |
| 2.0–2.55 | 9 | m | — |
| 1.25–1.40 | 2 | m | — |
| 1.0–1.1 | 3 | d | 6.5 |
| 0.75–0.85 | 3 | — | 5.5 |

EXAMPLE 163

4-(3-(4-Acetyl-3-hydroxy-2-propylphenoxy)propoxy)-3-fluoro-gamma-oxobenzenebutanoic acid.

EXAMPLE 164

4-(3-(4-Acetyl-3-hydroxy-2-propylphenoxy)propoxy)-gamma-oxobenzenebutanoic acid.

EXAMPLE 165

4-(3-(4-Acetyl-6-chloro-3-hydroxy-2-propylphenoxy)-2-methylidenepropoxy)-gamma-oxobenzenebutanoic acid

EXAMPLE 166

4-(3-(4-Acetyl-3-hydroxy-2-propylphenoxy)propylthio)-gamma-hydroxy-beta-methylbenzenebutanoic acid.

EXAMPLE 167

4-(3-(4-Acetyl-3-hydroxy-2-propylphenoxy)propylsulfonyl)-3-propyl-gamma-oxobenzenebutanoic acid.

EXAMPLE 168

4-(3-(4-Acetyl-3-hydroxy-2-propylphenoxy)propylthio)-3-propyl-gamma-oxobenzenebutanoic acid methyl ester.

EXAMPLE 169

(Beta S*, gamma R*) 4-(3-(4-acetyl-3-hydroxy-2-propylphenoxy)propylsulfonyl-3-fluoro-gamma-hydroxy-beta-methylbenzenebutanoic acid gamma lactone.

EXAMPLE 170

(Beta S*, gamma R*) 4-(3-(4-acetyl-3-hydroxy-2-propylphenoxy)propoxy)-3-bromo-gamma-hydroxy-beta-methylbenzenebutanoic acid gamma lactone.

EXAMPLE 171

(Beta R*, gamma S*) 4-(3-(4-acetyl-3-hydroxy-2-propylphenoxy)propylsulfonyl)-3-chloro-gamma-hydroxy-beta-methylbenzenebutanoic acid gamma lactone.

EXAMPLE 172

2-(3-(4-acetyl-3-hydroxy-2-propylphenoxy)propoxy)-3-fluoro-gamma-oxobenzenebutanoic acid.

What is claimed is:

1. A compound of the Formula:

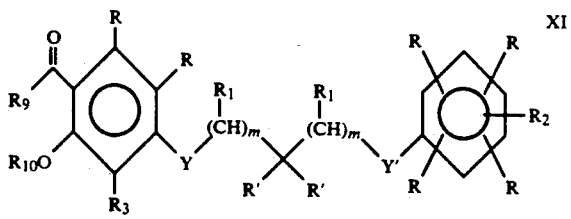

wherein:
each R is independently H, alkyl of 1 to 6 carbon atoms which may be straight chain or branched, alkenyl of 2 to 6 carbon atoms which may be straight chain or branched, trifluoromethyl, alkoxy of 1 to 6 carbon atoms which may be straight chain or branched, phenyl, phenyl substituted by alkyl of 1 to 3 carbon atoms or by halogen, benzyl, phenalkyl with from 2 to 4 alkyl carbon atoms, halogen, COOR₄, formyl, CN, trifluoromethylthio, or nitro;
each R' is independently R₄, OR₄, COOR₄, N(R₄)₂, SR₄, CH₂OR₄, CHO, CH₂, or together R' and R' are O;
each R₁ is independently hydrogen or alkyl of 1–3 carbon atoms;
R₂ is

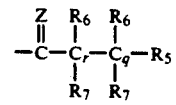

R₃ is H, alkyl of 3 to 6 carbon atoms which may be straight chain or branched, or alkenyl of 3 to 6 carbon atoms which may be straight chain or branched;
R₄ is H or alkyl of 1 to 6 carbon atoms which may be straight chain or branched;
R₅ is COOR₄, CH₂OH, CHO, tetrazole, NHSO₂R₁₄, CONHSO₂R₁₄, CN, or CON(R₇)₂;
each R₆ is independently H or alkyl of 1–4 carbons;
each R₇ is independently H, OH, or alkyl of 1–4 carbons;
R₉ is alkyl of 1 to 6 carbon atoms which may be straight chain or branched, alkoxy of 1 to 6 carbon atoms which may be straight chain or branched, or (CH₂)ᵣR₅;
R₁₀ is H, alkyl of 1 to 6 carbon atoms which may be straight chain or branched,

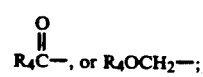

R₁₁ is alkyl of 1–4 carbon atoms which may be straight chain or branched;
R₁₂ is H or alkyl of 1–4 carbon atoms which may be straight chain or branched;
R₁₃ is alkyl of 1–4 carbon atoms which may be straight chain or branched or alkoxy of 1–4 carbon atoms which may be straight chain or branched;

$R_{14}$ is OH, alkyl or alkoxy of 1 to 6 carbon atoms, perhaloalkyl of 1 to 6 carbon atoms, phenyl or phenyl substituted by alkyl or alkoxy groups of 1 to 3 carbon atoms, halogen, hydroxy, haloalkyl, COOH, CN, formyl, or acyl of 1 to 6 carbon atoms;
Y is oxygen, sulfur, sulfoxide, sulfone

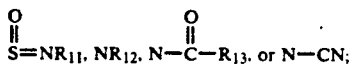

Y' is Y,

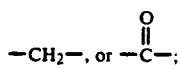

Z is O, S, $CH_2$, alkenyl of 1–4 carbons, or $N-R_{14}$;
each m is independently an integer from 0–6,
r and q are each independently 0–20, provided that the total of r and q does not exceed 20; and
p is 0 or 1;
or a pharmaceutically acceptable salt thereof.

2. A compound of claim 1 wherein Y is oxygen and Y' is oxygen, sulfur, sulfoxide, sulfone, amino, or cyanamido.

3. A compound of claim 1 wherein each m is 1.

4. A compound of claim 1 having the name:
4-((3-(4-Acetyl-3-hydroxy-2-propylphenoxy)propyl)-thio)-gamma-oxobenzenebutanoic acid,
4-((3-(4-Acetyl-3-hydroxy-2-propylphenoxy)propoxy)-3-fluoro-gamma-oxobenzenebutanoic acid,
4-((3-(4-Acetyl-3-hydroxy-2-propylphenoxy)propoxy-gamma-oxobenzenebutanoic acid,
4-((3-(4-Acetyl-3-hydroxy-2-propylphenoxy)propylsulfonyl)-gamma-oxobenzenebutanoic acid,
4-((3-(4-Acetyl-3-hydroxy-2-propylphenoxy)-2-hydroxypropyl)thio)-2-fluoro-gamma-oxobenzenebutanoic acid,
4-((3-(4-Acetyl-3-hydroxy-2-propylphenoxy)-2-hydroxypropyl)thio)-2-hydroxy-gamma-oxobenzenebutanoic acid,
4-((3-(4-Acetyl-3-hydroxy-2-propylphenoxy)propyl)-thio)-2-hydroxy-gamma-oxobenzenebutanoic acid,
4-((3-(4-Acetyl-3-hydroxy-2-propylphenoxy)-2-hydroxypropyl)thio)-2-methoxy-gamma-oxobenzenebutanoic acid,
4-((3-(4-Acetyl-3-hydroxy-2-propylphenoxy)propyl)-thio)-3-fluoro-gamma-oxobenzenebutanoic acid,
4-((3-(4-Acetyl-3-hydroxy-2-propylphenoxy)propyl)-thio)-2-fluoro-gamma-oxobenzenebutanoic acid,
4-((3-(4-Acetyl-3-hydroxy-2-propylphenoxy)propoxy)-3-fluoro-gamma-oxobenzenebutanoic acid,
4-((3-(4-Acetyl-3-hydroxy-2-propylphenoxy)propoxy)-2-fluoro-gamma-oxobenzenebutanoic acid,
4-((3-(4-Acetyl-3-hydroxy-2-propylphenoxy)propoxy)-gamma-oxobenzenebutanoic acid,
4-((3-(4-Acetyl-3-hydroxy-2-propylphenoxy)propoxy)-3-methyl-gamma-oxobenzenebutanoic acid,
4-((3-(4-Acetyl-3-hydroxy-2-propylphenoxy)propoxy)-2-chloro-gamma-oxobenzenebutanoic acid,
4-((3-(4-Acetyl-3-hydroxy-2-propylphenoxy)-2butenoxy)-3-fluoro-gamma-oxobenzenebutanoic acid,
4-((3-(4-Acetyl-3-hydroxy-2-propylphenoxy)-2hydroxypropylthio)-3-fluoro-gamma-oxobenzenebutanoic acid-S-oxide,
4-((3-(4-Acetyl-3-hydroxy-2-propylphenoxy)propylthio)-3-fluoro-gamma-oxobenzenebutanoic acid-S-oxide,
4-((3-(4-Acetyl-3-hydroxy-2-propylphenoxy)propylthio)-2-fluoro-gamma-oxobenzenebutanoic acid-S-oxide,
4-((3-(4-Acetyl-3-hydroxy-2-propylphenoxy)-2hydroxypropylthio)-2-fluoro-gamma-oxobenzenebutanoic acid-S-oxide,
4-((3-(4-Acetyl-3-hydroxy-2-propylphenoxy)propylsulfonyl)-2-fluoro-gamma-oxobenzenebutanoic acid,
4-((3-(4-Acetyl-3-hydroxy-2-propylphenoxy)-2-hydroxypropylsulfonyl)-2-fluoro-gamma-oxobenzenebutanoic acid,
4-((3-(4-Acetyl-3-hydroxy-2-propylphenoxy)propylsulfonyl)-3-fluoro-gamma-oxobenzenebutanoic acid,
4-((3-(4-Acetyl-3-hydroxy-2-propylphenoxy)-2-hydroxypropylsulfonyl)-3-fluoro-gamma-oxobenzenebutanoic acid,
4-((3-(4-Acetyl-3-hydroxy-2-propylphenoxy)-2-hydroxypropylsulfonyl)-gamma-oxobenzenebutanoic acid,
4-((3-(4-Acetyl-3-hydroxy-2-propylphenoxy)propoxy)-3-chloro-gamma-oxobenzenebutanoic acid,
4-((3-(4-Acetyl-3-hydroxy-2-propylphenoxy)-2-hydroxypropoxy)-3-fluoro-gamma-oxobenzenebutanoic acid, sodium salt, monohydrate,
4-((3-(4-Acetyl-3-hydroxy-2-propylphenoxy)propoxy)-alpha,alpha-dimethyl-gamma-oxobenzenebutanoic acid,
4-((3-(4-Acetyl-3-hydroxy-2-propylphenoxy)propoxy)-beta-methyl-gamma-oxobenzenebutanoic acid,
4-((3-(4-Acetyl-3-hydroxy-2-propylphenoxy)-2-methylidenylpropoxy)-gamma-oxobenzenebutanoic acid,
4-((3-(4-Acetyl-6-chloro-3-hydroxy-2-propylphenoxy)-2-methyidenepropoxy)-gamma-oxobenzenebutanoic acid,
4-((3-(4-Acetyl-3-hydroxy-2-propylphenoxy)-2-methyidenepropylthio)-gamma-oxobenzenebutanoic acid,
4-((3-(4-Acetyl-3-hydroxy-2-propylphenoxy)-2-methyidenepropoxy)-3-fluoro-gamma-oxobenzenebutanoic acid,
4-((3-(4-Acetyl-3-hydroxy-2-propyl-phenoxy)propylthio-gamma-oxobenzenebutyronitrile,
5-(3(4-(3-(4-Acetyl-3-hydroxy-2-propylphenoxy)propythio)phenyl)-3-oxopropyl)-1H-tetrazole,
4(3-(4-Acetyl-3-hydroxy-2-propylphenoxy)propylsulfonyl)-gamma-oxobenzenebutyronitrile,
5-(3(4-(3-(4-Acetyl-3-hydroxy-2-propylsufonylphenyl)-3-oxopropyl)-1H-tetrazole,
4-(3-(4-Acetyl-3-hydroxy-2-propylphenoxy)propylthio)-epsilon-oxobenzenehexanoic acid,
4(3-(4-Acetyl-3-hydroxy-2-propylphenoxy)propylsulfonyl)-epsilon-oxobenzenehexanoic acid,
4-(3-(4-Acetyl-3-hydroxy-2-propylphenoxy)-propylthio)-delta-oxobenzenebutanol,
4(3-(4-Acetyl-3-hydroxy-2-propylphenoxy)-propylsulfonyl)-delta-oxobenzenebutanol,
4-(3-(4-Acetyl-3-acetoxy-2-propylphenoxy)propylthio)-gamma-oxobenzenebutanoic acid,
4-(3-(4-Acetyl-3-acetoxy-2-propylphenoxy)-propylsulfonyl)-gamma-oxobenzenebutanoic acid,
4-(3-(4-Acetyl-3-hydroxy-2-propylphenoxy)propylsulfonyl)-gamma-oxobenzenebutyramide,
N-Methylsulfonyl 4-(3-(4-acetyl-3-hydroxy-2-propylphenoxy)propylthio-gamma-oxo-benzenebutyramide, 4-(3-(4-Acetyl-3-hydroxy-2-propylphenoxy)propyloxy)-gamma-oxo-beta,beta-dimethylbenzenebutanoic acid, 4-(3-(4-Acetyl-3-hydroxy-2-propyl-phenoxy)propyl)-thio)-gamma-oxobenzenebutanoic acid, 4-(3-(4-Acetyl-6-fluoro-3-hydroxy-2-propylphenoxy)-propyl)thio)-gamma-oxobenzenebutanoic acid, 4-(3-(4-Acetyl-6-chloro-3-hydroxy-2-propylphenoxy)-propyl)thio)-gamma-oxobenzenebutanoic acid, 4-(3-(4-Acetyl-6-chloro-3-hydroxy-2-propylphenoxy)-propylsulfonyl)-gamma-oxobenzenebutanoic acid, 4-(3-(4-Acetyl-6-bromo-3-hydroxy-2-propylphenoxy)-propyl)thio)-gamma-oxobenzenebutanoic acid, 4-(3-(4-Acetyl-6-bromo-3-hydroxy-2-propylphenoxy)-propylsulfonyl))-gamma-oxobenzenebutanoic acid, 4-(3-(4-Acetyl-3-hydroxy-6-methyl-2-propylphenoxy)-propyl)thio)-gamma-oxobenzenebutanoic acid, 4-(3-(4-Acetyl-3-hydroxy-2-propylphenoxy)propylthio)-3-propyl-gamma-oxo-benzenebutanoic acid, 4-(3-(4-Acetyl-3-hydroxy-2-propylphenoxy)propylsulfonyl)-3-propyl-gamma-oxobenzenebutanoic acid, 4-(3-(4-Acetyl-3-hydroxy-2-propylphenoxy)-propylsulfonyl)-gamma-oxo-beta,beta-dimethylbenzenebutanoic acid, 4-(3-(4-Acetyl-3-hydroxy-2-propylphenoxy)propylthio)-3-propyl-gamma-oxo-beta,beta-dimethylbenzenebutanoic acid, 4-(3-(4-Acetyl-3-hydroxy-2-propylphenoxy)propylthio)-3-fluoro-gamma-oxo-beta,beta-dimethylbenzenebutanoic acid sodium salt, 4-(3-(4-Acetyl-3-hydroxy-2-propylphenoxy)-propylthio)-3-chloro-gamma-oxo-beta,beta-dimethylbenzenebutanoic acid, 4-(3-(4-Acetyl-3-hydroxy-2-propyloxy-3-fluoro-gamma-oxo-beta,beta-dimethylbenzenebutanoic acid, 4-(3-(4-Acetyl-3-hydroxy-2-propylphenoxy)-propyloxy)-3-chloro-gamma-oxo-beta,beta-dimethylbenzenebutanoic acid, 4-(3-(4-Acetyl-3-hydroxy-2-propylphenoxy)-propyloxy)-3-bromo-gamma-oxo-beta,beta-dimethylbenzenebutanoic acid, 4-(3-(4-Acetyl-3-hydroxy-2-propylphenoxy)-propyloxy)-3-propyl-gamma-oxo-beta,beta-dimethylbenzenebutanoic acid, 3-(3-(4-Acetyl-3-hydroxy-2-propylphenoxy)-propylthio)-gamma-oxobenzenebutanoic acid, 3-(3-(4-Acetyl-3-hydroxy-2-propylphenoxy)-propylthio)-gamma-oxo-beta,beta,dimethylbenzenebutanoic acid, 3-(3-(4-Acetyl-3-hydroxy-2-propylphenoxy)-propyloxy)-gamma-oxo-beta,beta-dimethylbenzenebutanoic acid, 4-(3-(4-Acetyl-3-hydroxy-2-propylphenoxy)-propylsulfonyl)-3-propyl-gamma-oxobenzenebutanoic acid methyl ester, 4-(3-(4-Acetyl-3-hydroxy-2-propylphenoxy)-propylthio)-3-propyl-gamma-oxo-benzenebutanoic acid methyl ester, 4-(3-(4-Acetyl-3-hydroxy-2-propylphenoxy)-propylsulfonyl)-gamma-oxo-beta,beta-dimethylbenzenebutanoic acid, 4-(3-(4-Acetyl-3-hydroxy-2-propylphenoxy)propylthio)-3-propyl-gamma-oxo-beta,beta-dimethylbenzenebutanoic acid methyl ester, 4-(3-(4-Acetyl-3-hydroxy-2-propylphenoxy)propylthio)-3-fluoro-gamma-oxo-beta,beta-dimethylbenzenebutanoic acid, 4-(3-(4-acetyl-3-hydroxy-2-propylphenylthio)propyloxy)-3-fluoro-gamma-oxo-benzenebutanoic acid, 4-(3-(4-acetyl-3-hydroxy-2-propylphenylthio)propyloxy)-3-fluoro-gamma-oxo-benzenebutanoic acid S-oxide, 4-(3-(4-acetyl-3-hydroxy-2-propylphenylsulfonyl)-propyloxy)-3-fluoro-gamma-oxo-benzenebutanoic acid, 4-(3-(4-acetyl-3-hydroxy-2-propylthio)-gamma-oxo-benzenebutanoic acid, 4-(3-(4-acetyl-3-hydroxy-2-propylsulfonyl)propyloxy)-gamma-oxo-benzenebutanoic acid, 2-(3-(4-acetyl-3-hydroxy-2-propylphenoxy)propoxy)-3-fluoro-gamma-oxo-benzenebutanoic acid, 2-(3-(4-acetyl-3-hydroxy-2-propylphenoxy)propoxy)-3-fluoro-epsilon-oxobenzenebutanoic acid, or 4-(3-(4-acetyl-3-hydroxy-2-propylphenoxy)propoxy)-2,3-dichloro-gamma-oxobenzenebutanoic acid.

5. A pharmaceutical composition for antagonizing the leukotrienes in mammals, containing an effective amount of a compound of claim 1 and a pharmaceutically acceptable carrier.

6. A pharmaceutical composition of claim 5 wherein the mammal is a human.

7. A method of antagonizing leukotriene action in a mammal which comprises administering a compound of claim 1 to the mammal in a quantity effective to prevent leukotriene action or to inhibit leukotriene synthesis.

8. A compound of claim 1: wherein:
m is 1;
Y is oxygen; and
Y' is oxygen, sulfur, sulfoxide, sulfone, amino, or cyanamido.

9. A compound of claim 1 wherein:
Z is O, S, or N—$R_{14}$; and
r and q are each independently 0 to 5.

10. A compound of claim 1 wherein:
m is 1;
$R_1$ is H;
Y is oxygen;
Y' is oxygen, sulfur, sulfoxide, or sulfone;
each R' is independently $R_4$, $OR_4$, $CH_2OR_4$, or together R' and R' are O;
$R_2$ is $$-\overset{Z}{\underset{\|}{C}}-\underset{R_7}{\overset{R_6}{\underset{|}{(C)_r}}}-\underset{R_7}{\overset{R_6}{\underset{|}{(C)_q}}}-R_5$$

and is para to Y';
$R_3$ is alkyl of 1 to 6 carbon atoms which may be straight chain or branched;
$R_9$ is alkyl of 1 to 6 carbon atoms which may be straight chain or branched;
Z is O, S, or N—$R_{14}$; and
r and q are each independently 0 to 5.

11. A compound of claim 10 wherein $R_5$ is $COOR_4$.

12. A compound of claim 1 wherein:
m is 1;
R on the phenyl adjacent to Y' is H, alkyl of 1 to 6 carbon atoms which may be straight chain or branched, alkenyl of 2 to 6 carbon atoms which may be straight chain or branched, trifluoromethyl, alkoxy of 1 to 6 carbon atoms which may be straight chain or branched, thioalkyl of 1 to 6 carbon atoms which may be straight chain or branched, phenyl, phenyl substituted by alkyl of 1 to 3 carbon atoms or by halogen, benzyl, phenalkyl with from 2 to 4 alkyl carbon atoms, halogen, COOR$_4$, formyl, CN, trifluoromethylthio, or nitro;
Y is oxygen; and
Y' is oxygen, sulfur, sulfoxide, sulfone, amino, or cyanamido.

13. A compound of claim 12 wherein:
Z is O, S, or N—R$_{14}$; and
r and q are each independently 0 to 5.

* * * * *